United States Patent [19]

Bruynes et al.

[11] 3,945,994

[45] Mar. 23, 1976

[54] NOVEL ACID COMPOUNDS

[75] Inventors: Cornelis Adrianus Bruynes, Koudekerk ander Rijn; Johannes Karel van der Drift, Delft, both of Netherlands

[73] Assignee: Gist-Brocades N.V., Delft, Netherlands

[22] Filed: Feb. 5, 1974

[21] Appl. No.: 440,085

[30] Foreign Application Priority Data

Feb. 8, 1973    United Kingdom................ 6267/73

[52] U.S. Cl............ 260/239.1; 260/243 C; 424/246; 424/271
[51] Int. Cl.[2]....................................... C07D 499/68
[58] Field of Search................................ 260/239.1

[56]         References Cited
             UNITED STATES PATENTS 3,720,664   3/1973   Erickson.......................... 260/239.1

*Primary Examiner*—Gerald A. Schwartz
*Attorney, Agent, or Firm*—Hammond & Littell

[57]            ABSTRACT

Novel therapeutically useful and disinfecting penicillanic and cephalosporanic acid derivatives of the formula:

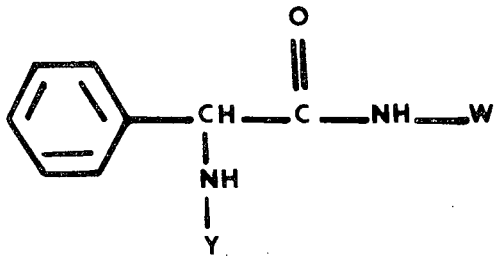

wherein W represents a penicillanic or cephalosporanic acid residue or derivatives thereof and wherein Y represents a carbonamido group N-substituted by a phosphorous or sulfur containing residue or Y represents a phosphorous or sulfur containing substituent, and pharmaceutical and disinfecting compositions containing them and their use and process for the preparation of the said compounds.

8 Claims, No Drawings

NOVEL ACID COMPOUNDS

OBJECTS OF THE INVENTION

It is an object of the invention to provide novel cephalosporanic and penicillanic acid compounds of formula I.

It is another object of the invention to provide a novel process for the preparation of the products of the invention.

It is a further object of the invention to provide novel antibacterial compositions.

It is an additional object of the invention to provide a novel method of combatting bacterial infection in warm-blooded animals.

These and other objects and advantages of the invention will become obvious from the following detailed description.

THE INVENTION

The novel penicillanic and cephalosporanic acid derivatives of the invention have the formula

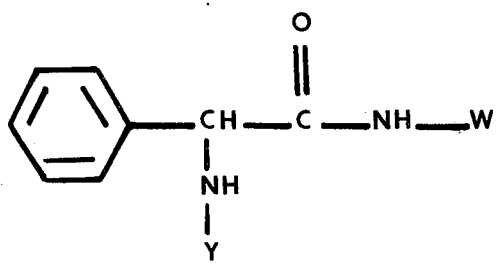

wherein W is a penicillanic or cephalosporanic acid residue of the formula:

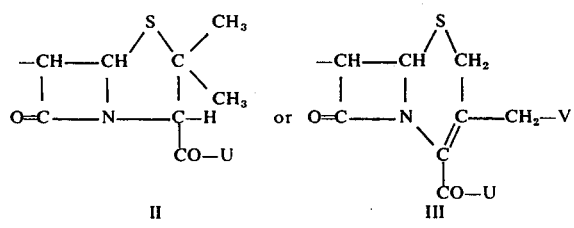

wherein U is an imido group (such as saccharinyl, phthalimido, succinimido) or a group —OE, E is hydrogen, a salt-forming cation, an ester-forming group which may be easily removed (such as by hydrolysis, by hydrogenation or by a substitution reaction using basic or nucleophilic agents), or E is an ester-forming group known to improve the absoprtion characteristics of penicillanic or cephalosporanic acid compounds after oral administration to a human or animal, V is selected from the group consisting of hydrogen, halogen, an azido, hydroxy, an amino, a carbamoyloxy, cyano, (lower)alkanoyloxy group (preferably acetoxy), an optionally substituted mononuclear heterocyclic group containing a sulfur or nitrogen atom, and preferably having 5 to 6 atoms in the ring (e.g. lutidinyl, picolinyl, pyridyl) and —S—Q (wherein Q is (lower)-alkenyl, benzyl, thienyl, furyl, diazolyl, triazolyl, tetrazolyl, thiazolyl, thiadiazolyl, thiatriazolyl, isoxazolyl, oxazolyl, oxadiazolyl, benzimidazolyl, imidazolyl, benzoxazolyl, triazolopyridyl or purinyl) optionally substituted with at most two lower alkyl or phenyl, Y is a substituent selected from the group consisting of (A) 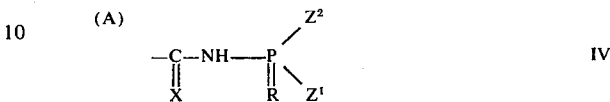 IV wherein X and R are individually taken from the group consisting of oxygen and sulfur, and $Z^1$ and $Z^2$ are individually selected from the group consisting of lower alkoxy, (lower)alkylthio, optionally substituted phenoxy, optionally substituted benzyloxy, optionally substituted amino group [e.g. mono(lower) alkylamino, mono-cycloalkylamino, di(lower)alkylamino, monophenylamino, mono(mono-nuclear heterocyclyl)amino, (lower) alkoxy-carbonyl-hydrazino, or (lower)acylhydrazino such as (lower)alkanoylhydrazino], optionally substituted(lower)alkyl, optionally substituted phenyl, hydroxy and OM, wherein M is a salt forming cation, or $Z^1$ and $Z^2$ form together with the phosphorous atom an optionally unsaturated 5 to 7 membered heterocyclic ring optionally substituted with at most four lower alkyl groups, (B)  V wherein $Z^3$ is (lower)alkyl, (lower)alkoxy, di(lower)alkylamino, amino, phenyl or hydroxy, and $Z^4$ is (lower)alkoxy, (lower) alkylthio, aryloxy, (e.g. phenoxy), or optionally substituted amino group [e.g. mono(lower)alkylamino, mono-cycloalkylamino, di(lower)alkylamino, mono-phenylamino, or mono-(mononuclear heterocyclyl)amino];

(C) 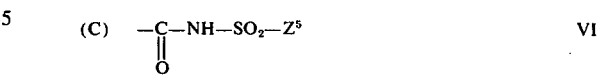 VI wherein $Z^5$ is

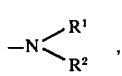, wherein $R^1$ is hydrogen or (lower)alkyl and $R^2$ is hydrogen, (lower)alkyl optionally substituted with an optionally esterified carboxy [e.g. (lower)alkoxycarbonyl(-lower)alkyl], phenyl, cycloalkyl or optionally substituted mono-nuclear heterocycle containing 5 to 7 atoms in the ring and containing hetero-atoms selected from oxygen, sulfur and nitrogen, an amino optionally substituted with (lower)alkyl, phenyl or (lower)alkoxycarbonyl, or $R_2$ is aryl (e.g. phenyl) or mononuclear heterocycle having one or more hetero atoms selected from oxygen, nitrogen and sulfur and containing 5 or 6 atoms in the ring [e.g. oxazolyl, oxadiazolyl, isoxazolyl, isothiazolyl, thiadiazolyl, thiazolyl and pyridyl optionally carrying one or more substituents], or $R^1$ and $R^2$ together with the nitrogen atom to which they are attached represent a mononuclear heterocyclic nucleus containing 5 or 6 atoms in the ring and having besides the nitrogen atom additional hetero atom(s) selected from oxygen, nitrogen and sulfur [e.g. morpholino, pyrrolidino, piperidino], or $Z^5$ is $X-R^3$ wherein X is as hereinbefore defined and $R^3$ is lower alkyl, or $Z^5$ is hydroxy or —OM wherein M is a salt-forming cation, e.g. an alkali metal atom, or

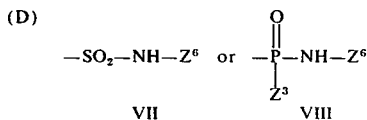

wherein $Z^6$ is hydrogen, —CO—$R^4$ in which $R^4$ is (lower)alkoxy, aryloxy e.g. phenoxy, (lower) alkylthio or arylthio, an optionally substituted amino —$NR^1R^2$, in which $R^1$ and $R^2$ are as hereinbefore defined, or

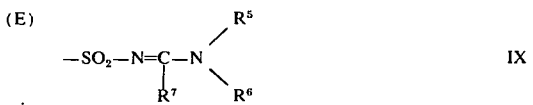

wherein $R^5$ and $R^6$ are the same or different and each is (lower)alkyl, phenyl or cycloalkyl or $R^5$ or $R^6$ together with $R^7$ and the "—C—N—" group represented a mononuclear heterocycle containing 5,6 or 7 atoms in the ring, or $R^5$ and $R^6$ together with the nitrogen atom to which they are attached are mononuclear heterocycle containing 5 or 6 atoms in the ring, and $R^7$ is hydrogen, (lower)alkyl, cycloalkyl or phenyl.

The term "lower" as applied herein to alkyl, alkoxy, alkylthio, alkoxycarbonyl, acyl and alkanoyl means that the group in question contains at most 6 carbon atoms. The term "cycloalkyl" indicates a carbocyclic ring of 5 to 8 carbon atoms. The substituents which may optionally be present on a phenyl nucleus or on a mononuclear heterocycle nucleus within the definition of Y are selected from halogen, nitro, cyano, di(lower)alkylamino, (lower) alkyl, (lower)alkoxy, optionally esterified carboxy, optionally substituted carbamoyl, (lower)acylamino [e.g. (lower)alkanoylamino] or (lower)alkoxycarbonylamino.

Ester groups, which may improve the physical absorption characteristics of the compounds of the formula I are selected from, for example, groups of the formula:

$$-CH_2-O-CO-R^8 \qquad XA$$

wherein $R^8$ is straight or branched chain alkyl of 1 to 8 carbon atoms optionally substituted by one or more substituents selected from lower (alkoxy), (lower)alkylthio, halo(lower) alkyl or nitro and halogen.

The salt-forming cations as indicated within the definition of symbol E and OM are those which form non-toxic, pharmaceutically acceptable salts of the compounds of formula I, such as sodium, potassium or other alkali metals, calcium or other alkaline earth metals or amines (e.g. tri(lower)alkylamine, procaine or benzylamine) salts. Hydrates of salts, possibly internal salts or zwitterionic modifications, of the compounds of formula I are included within the scope of the invention.

Examples of groups within formula IV are di(lower)alkoxyphosphinylaminocarbonyl, di(lower)alkoxyphosphinothioylaminocarbonyl, diphenoxyphosphinylaminocarbonyl, diphenoxyphosphinothioylaminocarbonyl, di[di(lower)alkylamino]phosphinylaminocarbonyl, di[di(lower)alkylamino]phosphinothioylaminocarbonyl, di(lower)alkylthiophosphinothioylaminocarbonyl, diphenylphosphinylaminocarbonyl, diphenylphosphinothioylaminocarbonyl, di(lower)alkylphosphinylaminocarbonyl, di(lower)alkylphosphinothioylaminocarbonyl, di(anilino)phosphinylaminocarbonyl, anilino-(lower)alkoxy-phosphinylaminocarbonyl, hydroxy-(lower)alkoxy-phosphinylaminocarbonyl, hydroxy-phenylphosphinylaminocarbonyl, hydroxy-(lower)alkylphosphinylaminocarbonyl, (lower)alkoxy-benzyloxyphosphinylaminocarbonyl, phenyl-benzyloxyphosphinylaminocarbonyl, lower alkyl-benzyloxyphosphinylcarbonyl, dibenzyloxy-phosphinylaminocarbonyl, dihydroxy-phosphinylaminocarbonyl, hydroxy-di(lower)alkylamino phosphinylaminocarbonyl, benzyloxy-di(lower)alkylamino phosphinylaminocarbonyl, di(lower)alkylthiophosphinylaminocarbonyl and (lower) alkoxycarbonylhydrazino(lower)alkoxy-phosphinylaminocarbonyl, the corresponding -phosphinyl (or phosphinothioyl) aminothiocarbonyl groups and the 3,4-dimethyl-1-oxo-3-phospholene-1-yl-aminocarbonyl group.

An example of a group within formula V is (lower) alkoxy-N'-phenylureido-phosphinyl.

Examples of groups within formula VI are (lower)-alkoxysulfonylaminocarbonyl, anilinosulfonylaminocarbonyl, di(lower)alkylaminosulfonylaminocarbonyl, mono(lower)alkylaminosulfonylaminocarbonyl, (lower)alkoxycarbonyl(lower)alkylaminosulfonylaminocarbonyl, pyridyl- or isoxazolylaminosulfonylaminocarbonyl optionally carrying one or more lower alkyl substituents on the heterocycle nucleus, benzylaminosulfonylaminocarbonyl, (5-methyl-1,2,4-oxadiazol-3-yl-methyl aminosulfonylaminocarbonyl, morpholinsulfonylaminocarbonyl, (lower)-alkoxycarbonylhydrazinosulfonylaminocarbonyl, aminosulfonylaminocarbonyl, and sulfoaminocarbonyl and alkali metal derivatives thereof.

Examples of groups within formula VII are aminosulfonyl, (lower)alkoxycarbonylaminosulfonyl, phenoxycarbonylaminosulfonyl.

Examples of groups within formula IX are di(lower)alkylamino-(lower)alkylidene-aminosulfonyl and 1-(lower)alkylpyrrolidin-2-ylidene-aminosulfonyl.

A preferred class of compounds of formula I is that wherein W is a penicillanic or cephalosporanic acid group, E is hydrogen, sodium, potassium or ammonium ions or a pharmaceutically acceptable ester-residue of formula XA, V is acetoxy, 5-methyl-1,3,4-thiadiazol-2-yl thio, pyridyl or azido, and Y is —CO—NH—$SO_3M'$ in which M' is hydrogen or a salt-forming, pharmaceutically acceptable cation such as an alkali metal (preferably sodium), or a group of —$SO_2$—$NH_2$ or

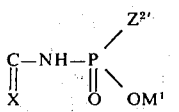

which X is oxygen or sulfur, $Z^{2'}$ is hydroxy, $OM^1$, (lower)alkoxy, phenoxy, di(lower)alkylamino, phenyl or (lower)alkyl group.

The compounds of formula I may be prepared by known methods for the preparation of structurally similar penicillins and cephalosporins using, for example, 6-(α-aminophenylacetamido) penicillanic acid [i.e. ampicillin], 7-(α-aminophenylacetamido) cephalosporanic acid [i.e. cephaloglycin], 7-(α-aminophenylacetamido) desacetoxycephalosporanic acid [i.e. cephalexin] and derivatives of these cephalosporins bearing otherwise substituted (3) methyl substituents as initial starting materials. Such starting materials have been known for a long time from a great variety of literature sources and are commercially available antibiotics. They may be prepared by many methods known in the art such as described in the U.S. Pat. Nos. 3,157,640; 3,140,282; 2,985,648; 3,487,073; 3,520,876 and 3,576,855; British Pat. Nos. 1,082,427; 1,199,186 and 1,270,633; German Offenlegensschriften Nos. 20,29,195; 19,45,607 and 2163,279; South African Pat. Nos. 67/5627 and 60/07577, and Belgian Pat. Nos. 726568, 726765 and 777262.

Thus according to another feature of the invention, the compounds of formula I are prepared by the process which comprises reacting a compound of the formula:

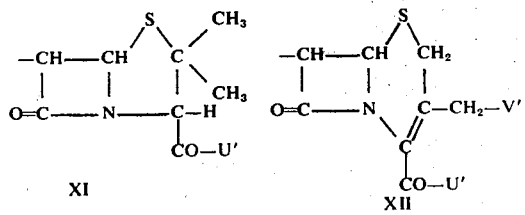

X wherein π is hydrogen, alkali metal, or a silyl such as a tri(lower alkyl)silyl or a tri(phenyl)silyl and $W'$ is a group of the formula

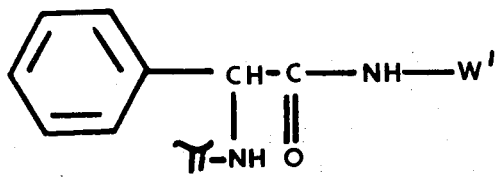

wherein $U'$ is an imido group or $-OE'$, $E'$ is an ester-forming protecting group, preferably one which can be easily removed after the reaction (e.g. by hydrolysis, hydrogenation or a substitution reaction using a basic or nucleophilic reagents) and which does not interfere with the reaction, and $V'$ has the same significance as defined above for the symbol V with the proviso that groups within the definition of V which may react or may be influenced under the reaction conditions have been adequately protected (e.g. by esterification or acylation) with a compound A1. of the formula:

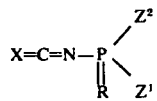

XIII wherein X, R, $Z^1$ and $Z^2$ are as defined above in an inert organic solvent at temperatures within the range from $-30°C$ to $30°C$, preferably under anhydrous conditions, optionally followed by removal of the protecting group $E'$ and any other protecting group(s) present from the compound so obtained; or B1. of the formula:

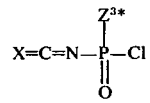

wherein $Z^{3=}$ has the same significance as $Z^3$ as defined above or is a group which can be easily converted to a group $Z^3$ and X is as defined above in an inert organic solvent at temperatures below 0°C, preferably between $-40°C$ and $-80°C$, preferably under anhydrous conditions, followed by reacting a compound so obtained with a compound of the formula $$Z^{4=} - H$$

wherein $Z^{4=}$ has the same significance as $Z^4$ or a group which can be easily transformed into a group after the reaction at temperatures below 25°C, preferably between $-40°C$ and $-80°C$, optionally in presence of an acid-binding agent such as an organic base and preferably under anhydrous conditions, optionally followed by removal of any protecting group(s); or C1. of the formula:

$$X = C = N - SO_2 - Cl$$

wherein X is as defined above in an inert organic solvent at temperatures below 0°C, preferably between $-40°C$ and $-80°C$, and preferably under anhydrous conditions, followed by reacting the compound so obtained with a compound of the formula:

$$Z^{5=} - H$$

wherein $Z^{5=}$ has the same significance as $Z^5$ as defined above or is a group which can easily be converted to a group $Z^5$ after the reaction at temperatures below 25°C and preferably between $-40°C$ and $-80°C$, optionally in the presence of an acid-binding agent such as an organic base (e.g. pyridine) and preferably under anhydrous conditions, optionally followed by the removal of any protecting group(s) present in the resulting product; or D1. of the formula:

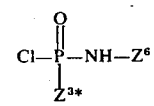

wherein $Z^6$ and $Z^{3=}$ have the same significance defined above in an inert organic solvent at temperatures below 35°C, preferably at about 0° – 10°C depending upon the character of the substituent optionally in the presence of an acid-binding agent such as an organic base (e.g. pyridine) and preferably under anhydrous conditions, optionally followed by removal of any protecting group(s) present in the resulting product; or E1. of the formula:

wherein K is —NH—$Z^6$ is as defined above or K is a group

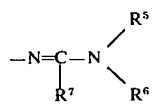

wherein $R^5$, $R^6$ and $R^7$ are as defined above in an inert organic solvent at temperatures below 35°C, preferably at about 0° – 10°C, optionally in the presence of an acid-binding agent such as an organic base (e.g. pyridine) and preferably under anhydrous conditions, optionally followed by removal of any protecting group(s) present in the resulting product.

The compounds of formula XVIII have been hitherto prepared by the conversion of a compound of the formula

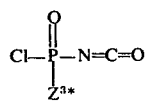

by the reaction with water, thiols, alcohols, carboxylic acids, amines etc by methods known per se.

Compounds of formula XX have been hitherto prepared by the conversion of a compound of the formula:

by reaction with water, thiols, alcohols, carboxylic acids, amines etc by methods known per se.

The reactions are carried out in an inert organic solvent such as dichloromethane, acetonitrile, ethyl acetate, benzene, toluene or mixtures thereof.

The starting materials of formula X having the carboxy group and optionally other reactive groups in the residues XI and XII suitably protected may be prepared by methods known per se.

For the protection of, for example, the carboxy group, preferably ester groups are used such as a silyl group having the formula $(R'')_3 \!\!>\!\!Si\!\!\sim\!\!or\ (R'')_2\!\!>\!\!Si\!\!<$ wherein R'' is (lower)alkyl, (lower)halosubstituted alkyl, aryl, aryl (lower)alkyl or lower alkoxy, an optionally substituted benzyl or benzhydryl, an optionally substituted (preferably halo-substituted) phenacyl, trichloroethyl, or a tert.-butyl. More preferably, silylesters of the residues of formulae XI and XII are used as starting materials, which are prepared by reacting compounds of formula X having a free carboxy group with, for example, N,O-bis (trimethylsilyl)acetamide, trimethylsilylacetamide, trimethylchlorosilane or dimethyldichlorosilane.

The starting compounds of the formulae XIII, XIV, XVIII, XIX and XX may be prepared by methods known per se, as described in, for example, R. Graf, Angew. Chem. 80, 179 (1968);
L. I. Samarai et al., Zh. Obshch. Khim. 39, 1511 (1969);
M. Kulka, Can. J. Chem. 37, 525 (1959);
J. Michalski et al., Roczniki Chem. 31, 585 (1957);
G. I. Derkach et al., Zh. Obshch. Khim. 38, 1784 (1968);
G. I. Derkach et al., Zh. Obshch. Khim. 35, no. 12, p. 2220 (1965);
E. S. Gubnitskaya et al., Zh. Obshch. Khim. 40, 1205 (1970);
L. I. Samarai et al., Zh. Obshch. Khim. 39, 1712 (1969);
A. V. Narbut et al., Zh. Obshch. Khim. 38, 1321 (1968);
G. Tomaschewski et al., Arch. Pharm. 301, 520 (1968), and
G. I. Derkach, Angew. Chem. 81, 407 (1969).

It will be appreciated that the optionally subsituted methyl on site 3 of the cephalosporanic acid nucleus may also be transformed into a more preferred substituted methyl in a subsequent reaction step after the above mentioned reactions with the amino group.

The new penicillanic and cephalosporanic acid derivatives of formula I have antibiotic properties which make them useful for human beings and animals, alone or mixed with other known medically active ingredients. Some of the new compounds of formula I have activities comparable with those of known β-lactam antibiotics and are especially active against gram positive microorganisms such as *Bacillus subtilis*, *Staphylococcus aureus*, *Strepococcus haemolyticus* and *faecalis*, and *Diplococcus pneumoniae*. They have, moreover, a good activity against penicillin-resistant Staphylococci, especially the compounds in which Y represents ~CS—

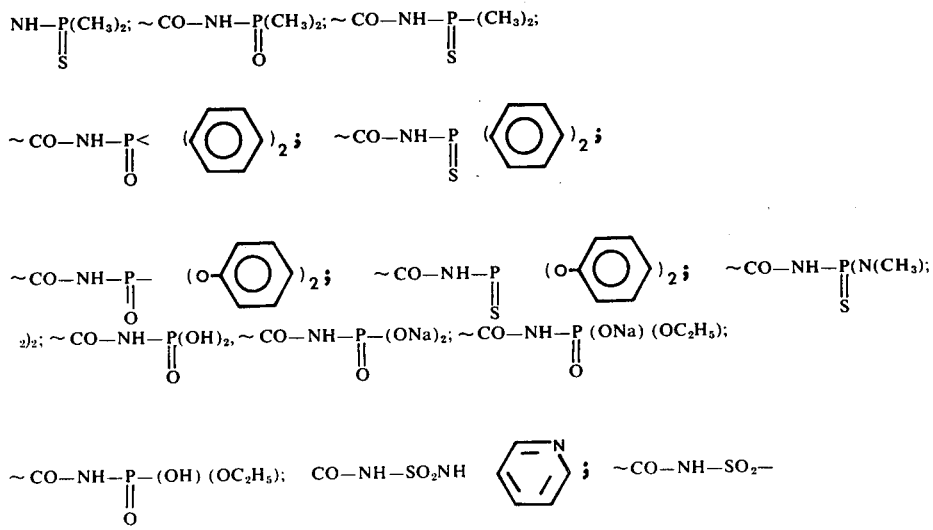

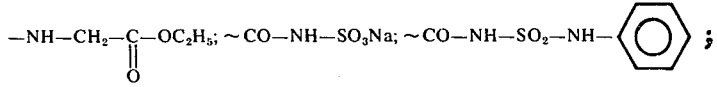

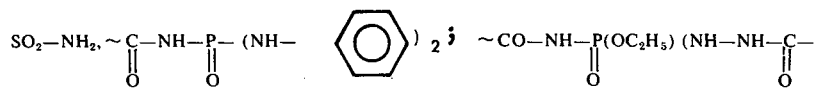

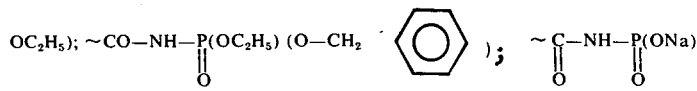

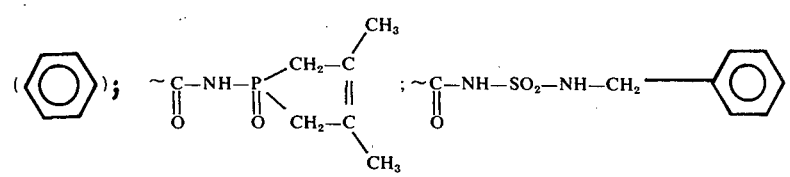

and

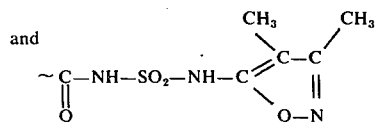

They are also active against Gram-negative microorganisms, e.g. *Brucella melitensis, Pasteurella multocida, Proteus rettgeri* and *Proteus mirabilis*.

The compounds according to the invention are preferably employed for therapeutic purposes in the form of an ester or a non-toxic, pharmaceutically acceptable salt such as sodium, potassium or calcium salt. Other salts that may be used include the non-toxic, suitably crystallizing salts with organic bases such as amines, for example trialkylamines, procaine and dibenzylamine.

In the treatment of bacterial infections, the compounds of this invention can be administered topically, orally or parenterally in accordance with conventional procedures for administration of antibiotics. They are administered in dosage units containing an effective amount of the active ingredient in combination with suitable physiologically acceptable carriers or excipients. The dosage units can be in the form of liquid preparations such as solutions, suspensions, dispersions or emulsions, or in a solid form such as powders, tablets and capsules.

Accordingly, the invention includes within its scope antibiotic compositions comprising an effective amount of a compound of formula I, or a non-toxic, pharmaceutically acceptable salt thereof, in association with a physiologically-acceptable carrier or excipient. Such therapeutic compositions can also include one or more therapeutically active ingredients in addition to a compound of the invention. The term "effective amount" as used herein in relation to the described compounds means an amount which is sufficient to destroy or inhibit the growth of susceptible microorganisms when administered in the usual manner, in other words an amount which is sufficient to control the growth of bacteria. The magnitude of an effective amount can be easily determined by those skilled in the art through standard procedures for determining the relative activity of antibacterial agents when utilized against susceptible microorganisms via the various available routes of administration.

Suitable carriers and excipients may be any convenient physiologically-acceptable ingredient which serves to facilitate administration of the therapeutically active compound. Carriers may provide some auxcillary function such as that of a diluent, flavor-masking agent, binding agent, action delaying agent or stabilizer. Examples of carriers include water, which can contain gelatin, acacia, alginate, dextran, polyvinylpyrrolidone or sodium carboxymethyl cellulose, aqueous ethanol, syrup, isotonic saline, isotonic glucose, starch, lactose, or any other such material commonly used in pharmaceutical and veterinary antibacterial compositions.

Another aspect of the invention includes a method for inhibiting the growth of bacteria by applying to the habitat of the bacteria an effective amount of the antibacterial compounds described herein. For example, the method can be applied to the treatment of bacterial infections in animals by administering to the host an effective amount of an antibacterial compound of the invention. The usual daily dose is 5 to 100 mg/kg depending upon the specific compound and the method of administration.

The novel penicillanic acid and cephalosporanic acid derivatives according to the formula I may be also used as growth promoters for ruminant animals such as cattle. They are also useful in in vitro applications, such as for disinfecting compositions at a concentration of about 0.1 to 1% by weight dissolved or suspended in a suitable inert carrier for application by washing or spraying.

EXAMPLE 1

Sodium D-6-[α-{3-(diethoxyphosphinyl)-thioureido}benzylcarbonamido]-penicillanate.

0.75 ml (about 3 mmol) of N,O-bis(trimethylsilyl)acetamide was added under anhydrous conditions, to a suspension of 1.05 g (3 mmol) of D(-) 6-α-amino-benzylcarbonamidopenicillanic acid (anhydrous D(-) ampicillin) in 50 ml of dry dichloromethane and after 30 minutes stirring at about 20°C, a clear solution was obtained. Then, a solution of 0.6 g (3 mmol) of diethoxyphosphinylisothiocyanate [$(C_2H_5O)_2$ P(O)NCS] in 10 ml of dichloromethane was added at 0°–5°C over a period of 10 minutes and as the reaction did not cause a rise in temperature, the reaction mixture was further stirred at 5°C for 150 minutes. A small amount of precipitate was formed and according to thin-layer chromatograms, ampicillin was no longer present in the reaction mixture. The reaction mixture was poured into 75 ml of ice-water and the pH was brought to 7.0. The layers were separated and as the organic layer did contain part of the desired penicillin, the aqueous layer was extracted once with 75 ml of ethyl acetate at pH 7.0. The organic layers were combined, concentrated to some extent in vacuo in order to remove dichloromethane, and subsequently treated with n-hexane until a precipitate was formed, which was vacuum filtered off, washed with n-hexane and dried in vacuo to constant weight to obtain 0.5 g (30%) of D-6-[α-{3-diethoxyphosphinyl)-thioureido}benzylcarbonamido]-penicillanic acid.

The aqueous layer still containing part of the desired acid was acidified to pH 3.0 at 0°C and was subsequently extracted three times with 25 ml of ethyl acetate. The combined extracts were washed once with a small volume of icewater, dried over anhyrous magnesium sulfate, filtered, concentrated in vacuo to small volume and treated with a concentrated solution of sodium α-ethylcapronate. The resulting precipitate was vacuum filtered, washed with cold diethyl ether and dried in vacuo to obtain 0.3 g (17%) of the monohydrate of the sodium salt of the said acid. This part of the product was slightly impure as it contained a small amount of sodium α-ethylcapronate.

IR of the sodium salt (KBr-disc, values in $cm^{-1}$): ± 3500, ± 3250, 1765, 1680, 1605, ± 1510, 1025 and 690.

PMR of the acid ($CDCl_3$, 60 Mc, δ-values in ppm, TMS as reference): 1.35 (further split triplet, J≈7 cps), 1.49 and 1.53 together 12H, about 3.9 to 4.5 (multiplet) and 4.39 (s) together 5H, about 5.4 to 5.75 (multiplet, $J_{AB}$≈4 cps, 2H), 5.97 (d, J≈6.5 cps, 1H), 7.0 (d, J≈8 cps, about 1H), 7.4 (5H), 7.8 (broad d, about 0.8H), 8.5 (broad), 9.5 (J≈6.5 cps, about 0.8H).

Using the same procedure, 17.3 mmol of redistilled diethoxyphosphinylisocyanate was reacted to obtain 7.7 g (78.5%) of sodium D-6-[α-{3-(diethoxyphosphinyl)-ureido}benzylcarbonamido]-penicillanate in the form of a colorless solid of at least 95% purity.

IR (KBr-disc, values in $cm^{-1}$): ± 3500, ± 3320, 1770, ± 1690, ± 1670, ± 1605, ± 1230, 1025, 690.

PMR ($d_6$-DMSO, 60 Mc,δ-values in ppm, 2,2-dimethylsilapentane-5-sulfonate (DSS) as reference): 1.2 (further split triplet, J≈7 cps) and 1.45 and 1.56 together 12H, about 3.75 to 4.3 (multiplet) and 4.05 (s) together 5H, about 5.25 to 5.7 (multiplet and together 3H), 7.35 (5H), 7.95 (d, J≈8.5 cps, 0.8H), about 8.8 (broad) and 9.1 (d, J≈7 cps) together about 1.5H.

Using the same procedure, 11.4 mmol of redistilled diethoxyphosphinothioyl isothiocyanate [$(C_2H_5O)_2P$(S)NCS] was used to obtain 5.5 g (80%) of sodium D-6-[α-{3-(diethoxyphosphinothioyl)-thioureido}-benzylcarbonamido]-penicillanate in the form of a colorless solid of at least 95% purity.

IR (ibidem): ± 3500, ± 3320, 1770, 1685, ± 1605, 1560, 1315, 1015.

PMR (ibidem): 1.25 (t, J≈7.1 cps) and 1.42 and 1.53 together 12H, 3.85 to 4.37 (octet, J≈7.1 cps and $J_{P-H}$≈9.2 cps) and 4.02 (s) together 5H, 5.1 to 5.55 (multiplet, 2H), 6.2 (d, J≈7.5 cps, 1H), 7.35 (5H), 9.1 to 9.35 (overlapping doublets, about 1.6H).

Using the same procedure, 18 mmol of redistilled diethoxyphosphinothioyl isocyanate [$(C_2H_5O)_2P$(S)NCO] was used to obtain 4.2 g (about 40%) of sodium D-6-[α-{3-diethoxyphosphinothioyl)-ureido}-benzylcarbonamido]-penicillanate in the form of a colorless solid of about 85–90% purity.

IR (ibidem): ± 3500, ± 3300, 3065 and 3035, 1765, 1670–1690, 1610, 1560 and 1530, 1020.

PMR (ibidem): 1.20 (t, J≈7.0 cps) and 1.23 (t, J≈7.2 cps) and 1.45 and 1.57 together 12H, 3.75 to 4.3 (at least 15 lines, presumably 2 octets) and 3.95 (s) together 5H, about 5.25 to 5.65 (m and d, 3H), 7.35 (5H), 7.95 (d, J≈8.5 cps, 0.8H), 9.15 (d, J≈7.0 cps, 0.8H).

EXAMPLE 2

Sodium D-6-[α-{3-(diphenoxyphosphinyl)-thioureido}-benzylcarbonamido]-penicillanate Using the method described by G. W. Kenner et al. [J. Chem. Soc., 673 (1953)], 2.35 g (30.9 mmol) of ammonium thiocyanate were added to a solution of 8.3 g (30.9 mmol) of diphenyloxyphosphinyl chloride [Cl—P(O) $(OC_6H_5)_2$] in a mixture of 25 ml of dry benzene and 25 ml of dry acetone and a precipitate of ammmonium chloride was formed immediately. The mixture was stirred for 4 hours at room temperature, held overnight at −15°C and then filtered under a nitrogen atmosphere. The solid obtained was washed with dry benzene and the washings were combined with the first filtrate.

30.9 mmol of anhydrous D(-) ampicillin suspended in dichloromethane were reacted with 30.9 mmol of N,O-bis(trimethysilyl)-acetamide using the procedure of Example 1. Subsequently, the solution of diphenyloxyphosphinyl isothiocyanate [$(C_6H_5O)_2P$(O)NCS] in a mixture of 25 ml of acetone and 75 ml of benzene was added at room temperature and the resulting slightly turbid, but colorless solution was additionally stirred for 30 minutes at room temperature. According to thin-layer chromatograms, ampicillin was virtually no longer present in the reaction mixture which contained one major reaction product and a small amount of a by-product. The reaction mixture was poured into 400 ml of ice-water and the pH of the resulting emulsion was adjusted to 6.8. Ethyl acetate was added until a clear two-layer system was obtained. In order to remove the by-product, the pH of the ice-cold mixture was adjusted to 8.0 and the layers were separated and the organic layer containing the by-product and part of the desired product was discarded. The aqueous layer was adjusted to pH 3.0 and was extracted with ethyl acetate. This extract was washed with a cold saturated sodium chloride solution, dried over anhydrous magnesium sulfate, filtered and concentrated to small volume. The sodium salt of the penicillanic acid product was obtained by addng a concentrated solution of sodium α-ethylcapronate in ethyl acetate and dry diethyl ether and the final product weighed 15.3 g (about 65%) and contained approximately 1 mole of ethyl acetate per mole of pencillin. .

IR (KBr-disc, values in cm$^{-1}$): ±3500, ±3270, 1770, 1680, ±1610, 1590, 1515, 1490, 1320, 1183 and 1158, 760 and 685.

PMR (d$_6$-DMSO, 60 Mc,δ-values in ppm, DSS as reference): 1.41 and 1.55 (6H), 4.13 (s, 1H), 5.35 to 5.6 (multiplet, 2H), 6.20 (d, J≈8 cps, 1H), about 7.05 to 7.5 (18H), 9.2 to 9.5 (overlapping doublets, about 1.6H).

Using the same procedure, 14.5 mmol of redistilled diphenoxyphosphinyl isocyanate was usd to obtain 8.9 g (92%) of sodium D-6-[α-{3-(diphenoxyphosphinyl)-ureido}-benzylcarbonamido]-penicillanate in the form of a colorless solid of at least 95% purity.

IR (ibidem): ±3500, ±3320, 1770, ±1680, ±1610, 1590 and 1490, 1525, 1185 and 1160, 685.

PMR (ibidem): 1.43 and 1.55 (6H), 4.06 (s, 1H), 5.25 to 5.75 m and d at ±5.65 (3H), about 7.0 to 7.6 (18H), 8.0 d, J≈8.5 cps, 0.8H), 9.1 (d, J≈7.5 cps, 0.8H).

Using the same procedure, 7.45 mmol of diphenoxyphosphinothioyl isothiocyanate [(C$_6$H$_5$O)$_2$P (S)NCS] as a solution in a benzene-acetone mixture, prepared in situ from ammonium thiocyanate and (C$_6$H$_5$O)$_2$P (S) Cl according to E. S. Levchenko and I. N. Zhmurova [Ukrain. Khim. Zhur. 22, 623 (1956)] were reacted to obtain 0.5 g (about 10%) of sodium D-6-[α-{3-(diphenoxyphosphinothioyl)-thioureido}-benzylcarbonamido]-penicillanate in the form of a slightly colored solid of about 80% purity (impurity: sodium α-ethylcapronate), but recovering 87.5% of (C$_6$H$_5$O)$_2$P (S) Cl.

IR (ibidem): ±3500, ±3330, 3380, 3060, 3030, 1765, 1675, ±1610, 1590, 1490, ±1510, ±1315.

PMR: (1:1 CDCl$_3$ and DMSO and some DCO$_2$D(N-H absorptions exchanged) 60 Mc,δ-values in ppm, TMS as reference): 1.45 and 1.57 (about 6H), 4.29 (s, 1H), 5.35 to 5.60 (AB-q, J≈4.1 cps, 2H), 6.18 (s, 1H), about 6.95 to 7.65 (about 18 H).

Using the same procedure, a solution of 10 mmol of diphenoxyphosphinothioyl isocyanate [(C$_6$H$_5$O)$_2$P (S) NCO] prepared in situ were reacted to obtain 5.4 g (79%) of sodium D-6-[α-{3-(diphenoxyphosphinothioyl)-ureido}-benzylcarbonamido]-penicillanate in the form of a colorless solid of at least 95% purity.

KBr (ibidem): ±3500, ±3320, 3060, 3035, 1765, ±1670, ±1600, ±1515, 1490, 1183, 1158.

PMR (d$_6$-DMSO, etc.): 1.44 and 1.56 (6H), 4.06 (s, 1H), 5.3 to 5.8 m and at 5.7 (d, J≈7.0 cps, 3H), about 6.95 to 7.6 (18H), 7.95 (d, J≈8.0 cps, 0.8H), 9.05 (d, J≈7.0 cps, 0.8H).

EXAMPLE 3

Sodium D-6-[α-{3-(bisdimethylaminophosphinyl)-thioureido}-benzylcarbonamido]-penicillanate Using the method described by J. Michalski et al. [Roczniki Chem. 31, 879 (1957)], 30 mmol of ammonium thiocyanate were reacted with 30 mmol of bisdimethylaminophosphinyl chloride (Cl-P(O)[N(CH$_3$)$_2$]$_2$) in a mixture of acetone and acetonitrile and after completion of the reaction, ammonium chloride was vacuum filtered off. The volume of the filtrate was increased with 75 ml of dry benzene and the resulting solution of bis(dimethylamino)phosphinyl isothiocyanate (N(CH$_3$)$_2$]$_2$-P(O)NCS) was conentrated in vacuo to about 30 ml.

Then, the solution, prepared as described above, was added over a period of 5 minutes at 10°–15°C. to a solution prepared by the reaction of 10.5 g (30 mmol) of D(−) ampicillin and 30 mmol of N,O-bis(trimethylsilyl)-acetamide in 150 ml of dichloromethane as described before. The resulting reaction mixture was additionally stirred for 30 minutes at 15°C and a rather good conversion was indicated by thin-layer chromatograms. The reaction mixture was poured into 400 ml of ice-water and the layers were separated at pH 7.4, after addition of ethyl acetate. The organic layer was twice extracted with cold water buffered to pH 8.0 and the organic layer was discarded. The combined aqueous layers were extracted once at pH 6.0 with ethyl acetate to remove a by-product and the desired product dissolved in ethyl acetate was obtained by extraction of the remaining aqueous layer at pH 3.0. The extract was washed with a saturated solution of sodium chloride in ice-water, dried over anhydrous magnesium sulfate after treatment with activated carbon, vacuum filtered, concentrated to small volume and treated with a concentrated solution of sodium α-ethylcapronate in ethyl acetate. The sodium salt of the penicillanic acid product was precipitated by addition of dry diethyl ether. The precipitate was collected by filtration, washed with diethyl ether and dried in vacuo to constant weight to obtain 4.3 g (about 29%) of the desired sodium salt in the form of a colorless solid of at least 95% purity.

IR (KBr-disc, values in cm$^{-1}$): ±3500, ±3230, 3060, 3032, 1770, 1685, ±1605, ±1520, ±1300, 990.

PMR (d$_6$-DMSO, 60 Mc, δ-values in ppm, DSS as reference): 1.42 and 1.54 (6H), 2.49, 2.52, 2.67 and 2.70 (4 lines, presumably 2 d with J$_{P-H}$ = 10.8 cps and J$_{P-H}$ = 10.6 cps, 12H), 4.12 (s, 1H), about 5.25 to 5.6 (multiplet, 2H), 6.23 (d, J≈7.2 cps, 1H), about 7.35 (5H), 9.2 (d, J≈7 cps), and about 9 (broad) together about 2H.

After addition of 1 droplet of DCO$_2$D the NH absorption was split in two relatively sharp doublets at about 10.2 and 9.3 ppm and a broad absorption at about 9 ppm.

Using the same procedure, 3.5 mmol of bis(dimethylamino) phosphinyl-isocyanate ([N(CH$_3$)$_2$]$_2$P(O)NCO), freshly prepared from N,N,N',N'-tetramethylphosphorotriamide and phosgene according to P. H. Terry and A. B. Borkovic [J. Med. Chem., 10, 118 (1967)] were reacted to obtain 0.7 g (42%) of sodium D-6[α-{3-(bisdimethylaminophosphinyl)-ureido}-benzylcarbonamido]-penicillanate in the form of a colorless solid of about 95% purity.

IR (ibidem): ±3500, ±3300, 2815, 1770, ±1675, 1610, ±1520, 1300, 1190 and 990.

PMR (ibidem): 1.45 and 1.57 (6H), 2.49 and 2.66 (2 narrow doublets, 12H), 3.96 (s, 1H), about 5.25 to 5.7 (multiplet 3H), about 7.35 (5H), about 7.95 to 8.3 (2 d, about 1.8 H), 8.95 (d, 0.8H).

Usng the same procedure, 26.3 mmol of redistilled but impure bis(dimethylamino)phosphinothioyl isothiocyanate ([N (CH$_3$)$_2$]$_2$P(S)NCS), prepared according to Houben Weyl 12$^{1,2,}$ 774,775 were reacted to obtain 5.2 g (about 38%) of sodium D-6-[α-{3-(bisdimethylaminophosphinothioyl)-thioureido}-benzyl-carbonamido]-penicillanate in the form of a slightly colored solid of 90–95% purity.

IR (ibidem): ±3500, ± 3185, about 3350, 2810, 1765, 1690, 1605, ± 1515, ±1315, 985, 738 and 690.

PMR (ibidem): 1.42 and 1.54 (6H), and 2.50 and 2.71 (2 narrow d, $\delta$,)≈1 cps, $J_{P-H}$≈12.3 cps, 12H), 3.95 (s, 1H), 5.25 to 5.55 (multiplet, $J_{5,6}$≈4.1 cps, 2H), 6.26 (d, J≈7.7 cps, 1H), about 7.4 (5H), 9.15 (d, J≈7.2 cps, 0.8H), 9.55 (d, J≈7.7 cps, 0.8H).

Using the same procedure, 10 mmol of crude bis(-dimethylamino)phosphinothioyl isocyanate ([N(CH$_3$)$_2$]$_2$P(S)NCO) dissolved in a mixture of 15 ml toluene and 25 ml of dichloromethane were reacted to obtain 0.28 g (5%) of the practically pure sodium D-6-[α-{3-(bis(dimethylamino)phosphinothioyl)-ureido}-benzylcarbonamido]-penicillanic acid and from the filtrate 1.3 g (about 20%) of the corresponding sodium salt of estimated 90–95% purity.

IR (ibidem): ±3500, ± 2550, ± 3240, ± 3350, 1780, ± 1730, ± 1705, ± 1680, ± 1655, ± 1520, 985, 740 and 700.

PMR (ibidem): 1.43 and 1.57 (6H), 2.45, 2.48, 2.66 and 2.69 (4 lines, 2 d with almost equal $J_{P-H}$= 12.5 cps, 12H), 4.21 (s, 1H), 5.45 (multiplet, $J_{56}$≈ 4.0 cps) and 5.56 (d, J≈7.5 cps) together 3H, about 7.35 and 7.55 (d, J≈7.5 cps) and 7.8 (d, J≈9.0 cps) together 7 to 7.5 H.

EXAMPLE 4

Sodium D-6-[α-{3-(diphenylphosphinothioyl)-thioureido}-benzylcarbonamido]-penicillanate Using the method described by Boedeker [Z. Chem., 11, 463 (1971)], 2.52 g (10 mmol) of diphenylphosphinothioyl chloride [(C$_6$H$_5$)$_2$P(S)Cl] and 0.76 g (10 mmol) of ammonium thiocyanate (NH$_4$CNS) in 10 ml of acetone were heated for 10 minutes on a steam bath resulting in the precipitation of a white solid and the mixture was diluted with 25 ml of dichloromethane. The mixture was then added to a solution of 10 mmol of the trimethylsilyl ester of D(=) ampicillin [prepared as in Example 1] in 25 ml of dichloromethane at 22°C. After 2 hours additional stirring at room temperature, thin-layer chromatograms indicated a good conversion to one major reaction product and a small amount of a by-product. While maintaining the pH at 7.0 the reaction mixture was poured into ice-water and the dichloromethane was removed in vacuo. Diethyl ether was added and the layers were separated. The aqueous layer was once more purified by extraction with diethyl ether at pH 7.0 and subsequently acidified to pH 3.5. A few extractions with ethyl acetate resulted in practically complete removal of the desired compound from the aqueous layer and the acid extracts were combined, washed with a saturated solution of sodium chloride in ice-water, dried over anhydrous magnesium sulfate, filtered, concentrated in vacuo to small volume and treated in the usual manner with sodium α-ethylcapronate and diethyl ether to give 5.35 g (about 80%) of the above-mentioned sodium salt in the form of a colorless, nearly pure solid.

IR (KBr-disc, values in cm$^{-1}$): ± 3500, ±3200, 3057, 1770, 1685, 1610, 1590 and 1490, ± 1515, 1305, 1438, 718 and 685.

PMR (d$_6$-DMSO, 60 Mc, $\delta$-values in ppm, DDS as reference): 1.41 and 1.52 (6H), 4.07 (s, 1H) about 5.25 to 5.65 (multiplet, 2H), 6.14 (d, J≈6.8 cps, 1H), about 7.3 and from about 8.2 to about 7.2 together about 15H, 9.2 (d, J≈7 cps) and 9.45 (d, J≈8 cps) together about 1.8H.

Using the same procedure, 22.4 mmol of crude diphenylphosphinothioyl isocyanate [(C$_6$H$_5$)$_2$P(S)NCO] prepared according to L. I. Samarai et al [J. Gen. Chem. USSR, 39, 1678 (1969)] were reacted to obtain 3.1 g (21%) of sodium D-6-[α-{3-(diphenylphosphinothioyl)-ureido}-benzylcarbonamido]-penicillanate in the form of a nearly pure, colorless solid.

IR (ibidem): ± 3500, 3200–3400, 3055, 1765, ± 1670, ± 1685, 1605, ± 1520, 1435, 720, 690.

PMR (ibidem): 1.44 and 1.57 (6H), 3.98 (s, 1H), about 5.25 to 5.7 (multiplet, 3H), centre at 7.35 and from about 8.25 to about 7.3 together 16–17 H, 9.05 (d,J ≈ 7 cps, 0.8H).

Using the same procedure, 18.9 mmol of redistilled diphenylphosphinyl isothiocyanate [(C$_6$H$_5$)$_2$P(O)NCS] were reacted to obtain 9.0 g (about 70%) of sodium D-6-[α-{3-(diphenylphosphinyl)-thioureido}-benzylcarbonamido]-penicillanate in the form of a colorless solid of about 90% purity.

IR (ibidem): ±3500, ± 3380, ± 3260, 3050, 1765, 1680, 1605, ± 1515, 1495, ± 1320.

PMR (ibidem): 1.43 and 1.54 (6H), 4.00 (s, 1H), about 5.2 to 5.6 (multiplet, 2H), 6.15 (d, 1H), centre at about 7.3 and from about 8.15 upwards together about 15H, about 9.0 (broad) and 9.2 (d) together about 1.5H, 9.8 (d, 0.7H).

Using the same procedure, 19 mmol of redistilled diphenylphosphinyl isocyanate [(C$_6$H$_5$)$_2$P(O)NCO] were reacted to obtain 9.0 g (75%) of sodium D-6-[α-{3-(diphenylphosphinyl)ureido}-benzylcarbonamido]-penicillanate in the form of a practically pure, colorless solid.

IR (ibidem): 3150 to 3550, 3060, 1765, 1675 and 1685, 1610, ± 1520, 1495, 1438, ± 1185.

PMR (ibidem): 1.44 and 1.45 (6H), 3.99 (s, 1H), from about 5.25 to 5.7 (multiplet, 3H), centre at about 7.35 and an extended multiplet, and about 8.1 (d), together about 16.5H from about 8.25 to 7.1, 9.05 (d. J≈7 cps, 0.9H).

EXAMPLE 5

Sodium D-6-[α-{3-(dimethylphosphinothioyl)-thioureido}-benzylcarbonamido]-penicillanate Partially dissolved dimethylphosphinothioyl isothiocyanate [(CH$_3$)$_2$P(S)NCS] was prepared by the addition of a solution of 2.57 g (20 mmol) of dimethylphosphinothioyl chloride [(CH$_3$)$_2$P(S)Cl] in 10 ml of acetone to 1.52 g (20 mmol) of ammonium thiocyanate (NH$_4$CNS) partially dissolved in 5 ml of acetone which resulted directly in the formation of a precipitate. After refluxing for 10 minutes, the contents of the flask were added all at once to a solution of the trimethylsilyl ester of D(–) ampicillin in 50 ml of dichloromethane prepared in the usual manner from 20 mmol of D(–) ampicillin and an equivalent amount of N,O-bis(trimethylsilyl)acetamide. A substantial rise in temperature was noticed and the reaction mixture was stirred additionally for 30 minutes and then was poured into ice-water of pH 7.0. After removal of low-boiling organic solvent in vacuo, diethyl ether was added and the resulting layers were separated. The aqueous layer was additionally purified by two extractions with a small volume of diethyl ether at pH 7.0, subsequently acidified to pH 4.0, and repeatedly extracted with diethyl ether. The combined acid ethereal extracts were washed once with a cold, saturated solution of sodium chloride in water, dried over anhydrous magnesium sulfate, filtered, and treated with a solution of sodium α-ethylcapronate in ethyl acetate. The isolated above named sodium salt weighed 8.3 g (76% yield).

IR (KBr-disc, values in cm$^{-1}$): ± 3480, ± 3300, 1770, ± 1680, 1605, ± 1520, 1320.

PMR: (d$_6$-DMSO, 60 Mc, δ-values in ppm, DSS as reference): 1.44 and 1.54 (6H), 2.02 and 2.25 (2 narrow doublets, J$_{P-H}$ = 14 cps, 6H), 4.01 (s, 1H), about 5.25 to 5.6 (multiplet, 2H), 6.18 (d, J≈6.5 cps, 1H); about 7.35 (5H), 9.15 (d, J≈6.5 cps), 9.6 (d, J≈7 cps).

Using the same procedure, 28.5 mmol of crude, impure dimethylphosphinyl isocyanate [(CH$_3$)$_2$P(O)NCO] were reacted to obtain 75% D(−)ampicillin as its hydrochloride salt and 1 g of sodium D-6-[α-{3-(dimethylphosphinyl)-ureido}-benzylcarbonamido]-penicillanate (7%) with a purity of at least 90%.

IR (ibidem): 3200–3600, 1765, ± 1670, 1605, ± 1525.

PMR (ibidem): 1.43 and 1.55 (6H), 2.03 and 1.79 (centres of 2 narrow doublets with δυ= 1.4 cps each, J$_{P-H}$ = 14.1 cps, 6H), 4.00 (s, 1H), about 5.4 (centre of multiplet) and 5.60 d, J≈8.2 cps) together 3H, about 7.35 (5H), 7.75 (d, J≈8.0 cps) and about 8.0 (broad) together about 1.4H, 9.0 (d, J≈7.5 cps, 0.8H).

Using the same procedure, 15 mmol of ampicillin and a solution of dimethylphosphinothioyl isocyanate [(CH$_3$)$_2$P(S)NCO] in a 1:1 mixture of dichloromethane and chloroform were reacted and after the reaction, much ampicillin was still present. Yield of sodium D-6-[α-{3-(dimethylphosphinothioyl)-ureido}-benzylcarbonamido]-penicillanate was 0.8 g (about 10%) with a purity of about 85%.

IR (ibidem): 3200–3600, 1765, ± 1670, 1605, ± 1530.

Further possibly characteristic absorptions (also present in the compound of the preceding Example above) 1435, 1410, 1320, 1225, 1125, 955, 925, 735 and 700.

PMR (ibidem): 1.45 and 1.56 (6H), 1.78 and 2.02 (centres of two narrow doublets with δυ= 1.0 cps each, J$_{P-H}$ = 14.1 cps, 6H), 3.96 (s, 1H), about 5.4 (centre of multiplet) and 5.60 (d, J≈8 cps) together 3H, about 7.35 (5H), 8.0 (d, J≈8 cps, 0.8H), 9.0 (d, J≈8 cps) and about 8.8 (broad) together about 1.4H.

EXAMPLE 6

Sodium D-6-[α-{3-(ethoxysulfonyl)-ureido}-benzylcarbonamido]-penicillanate.

Employing anhydrous conditions, 2.45 ml (about 10 mmol) of N,O-bis(trimethylsilyl)acetamide were added to a suspension of 3.49 g (10 mmol) of D(−) ampicillin in 75 ml of dry dichloromethane. After 30 minutes of additional stirring at room temperature, the temperature of the solution was lowered to about −60°C followed by the dropwise introduction of a solution of 0.86 ml (10 mmol) of chlorosulfonyl isocyanate (ClSO$_2$NCO) in 10 ml of dichloromethane at −60°C. The solution was additionally stirred for 30 minutes at −60°C followed by the introduction of 1 g of pyridine (12.5 mmol). As soon as the well stirred solution had been recooled to −60°C, 30 ml of anhydrous ethanol were added. The cooling bath was removed and the solution was stirred until the temperature had increased to 0°C. The reaction mixture was poured into 100 ml of ice-water, while dilute sodium hydroxide was simultaneously added to keep the pH close to 7.0. The layers were separated and the organic layer discarded and the aqueous layer was washed twice with dichloromethane. The remaining aqueous layer was acidified to pH 5.3 and was extracted once with a 1:1 mixture of diethyl ether and ethyl acetate to remove a by-product. The desired product was extracted at pH 4.2 with ethyl acetate and the extract was washed with a small amount of ice-water, dried over anhydrous magnesium sulfate, filtered, concentrated to small volume and treated with a concentrated solution of sodium α-ethylcapronate in ethyl acetate, followed by the addition of diethyl ether. After drying, the isolated solid above named sodium salt weighed 1.05 g (19%) with a purity of about 90%.

IR (KBr-disc, values in cm$^{-1}$): ± 3475, 3350, 3060, 1775, ± 1675, 1605, 1520, 1368 and 1170.

PMR (d$_6$-DMSO, 220 Mc, δ-values in ppm, DSS as reference): 1.43 and 1.57 (6H), 1.18 (t, J = 7.1 cps, 3H), 3.97 (t, J = 7.1 cps (2H)), 4.11 (s, 1H), ±5.29 (d, J = 4.0 cps, 1H), ± 5.45 (q, J = 4.0 cps and J′≈8.0 cps) and 5.50 (d, J≈7.5 cps) together 2H, about 7.3 (multiplet, 5H), 8.48 (s), 9.00 (d, J≈7.5 cps), 9.25 (d, J≈8.0 cps).

EXAMPLE 7

Sodium D-6-[α-{3-(phenylaminosulfonyl)-ureido}-benzylcarbonamido]-penicillanate

Starting with 10 mmol of D(−) ampicillin, the reaction was performed in the same way as in Example 6 up to the additional stirring period after the addition of chlorosulfonyl isocyanate which was reduced to 10 minutes. Subsequently, a solution of 3.5 ml (about 35 mmol) of redistilled aniline in 20 ml of dichloromethane was added as quickly as possible but continuously at about −60°C. Immediately thereafter, the temperature was allowed to rise gradually to 0° by removal of the cooling bath and with the simultaneous addition of dilute sodium hydroxide, the reaction mixture was poured into 100 ml of ice-water. The layers were separated at pH 7.0; the organic layer was discarded and the aqueous layer was washed once with dichloromethane and once with diethyl ether. The aqueous layer was extracted with a 1:1 mixture of diethyl ether and ethyl acetate at pH 5.2 to removal a by-product which caused the loss of a small part of the desired compound. The remaining aqueous layer was extracted at pH 4.5 with ethyl acetate and the extract was washed once with a small volume of ice-water, treated with activated carbon, dried over anhydrous magnesium sulfate, filtered, concentrated in vacuo to small volume and treated with a concentrated solution of sodium α-ethylcapronate in diethyl ether. After washings with cold diethyl ether and extensive drying, the final above named sodium salt weighed 3.72 g (63%) with a purity of 90–95%.

IR (KBr-disc, values in cm$^{-1}$): ± 3500, ± 3350, 3065, 1765, ± 1675, ± 1600, ± 1515, 1495, 1320, 1160, 1128,750 and 690 PMR [d$_6$-DMSO, 60 Mc, δ-values in ppm, DSS as reference): 1.44 and 1.56 (6H), 4.02 (s, 1H), about 5.4 (multiplet) and 5.56 (d, J≈8 cps) together 3H, about 6.7 to 7.5 (intensive absorptions at 7.28 and 7.15, 11–12H), 9.0 (d, J≈6.5 cps, 0.7H), 9.35 (s, about 0.4H).

EXAMPLE 8

Sodium D-6-[α-{3-(diisopropylaminosulfonyl)-ureido}-benzyl-carbonamido]-penicillanate Starting with 10 mmol of D(−) ampicillin, the reaction was carried out in the same way as in Example 7. An excess of diisopropylamine (35 mmol) was employed and after the reaction mixture had been poured into ice-water, the pH was 9.0 indicating that the excess of diisopropylamine could have been too large. After lowering the pH to 7.0, the layers were separated, the organic layer was discarded and the aqueous layer was purified by extractions with dichloromethane and diethyl ether. The desired product was obtained by extraction at pH 5.2 with a 1:1 mixture of diethyl ether and ethyl acetate to obtain 0.74 g (12%) of the practically pure, colorless above named sodium salt.

IR (KBr-disc, values in cm$^{-1}$): ± 3500, ± 3350, 1770, 1680, ± 1610, ± 1520, 1330 and 1130.

PMR (d$_6$-DMSO, 60 Mc, δ-values in ppm, DSS as reference): 1.18 (d, J = 6.6 cps, 12H), 1.43 and 1.54 (6H), 3.81 (centre of extended multiplet) and 3.96 (s) together 31 H, about 5.4 (multiplet) and 5.60 (d, J ≈ 8.0 cps) together 3H, about 7.35 (5H), 7.75 (d, J≈8.0 cps, 0.6H), 9.0 (d, J≈6.5 cps, 0.6H).

EXAMPLE 9

Sodium D-6-[α-{3-(isopropylaminosulfonyl)-ureido}-benzyl-carbonamido]-penicillanate.

Starting with 10 mmol of D(−) ampicillin, the reaction was carried out in the same way as in Example 7. The introduced amount of isopropylamine was 22 mmol and the reaction mixture was additionally stirred for one hour at 0°C and was subsequently poured into 100 ml of ice-water at pH 7.0. To remove by-products, the aqueous layer was repeatedly washed at pH 7.0 with dichloromethane and diethyl ether. The aqueous layer was finally extracted with ethyl acetate at pH 5.0 and this extract gave the above named penicillin salt contaminated with 10–15% of a by-product in a yield of 1.5 g (about 25%).

IR (KBr-disc, values in cm$^{-1}$): ± 3500, ± 3325, 1765, ± 1675, 1605, ± 1520, ± 1320 and 1158.

PMR (d$_6$-DMSO, 60 Mc, δ-values in ppm, DSS as reference): 1.08 (d, J = 6.5 cps, ±6H), 1.44 and 1.56 (6H), about 3.5 (multiplet, ± 1H), 4.02 (s, 1H), about 5.4 (multiplet) and 5.61 (d, J≈8.0 cps) together ±3H), about 7.35 (5H), 7.65 (d, J≈8.0 cps, 0.6H), 9.05 (d, J≈6.8 cps. 0.6H).

EXAMPLE 10

Sodium D-6-[α-{3-(ethoxycarbonylmethylaminosulfonyl)-ureido}-benzylcarbonamido]-pencillanate 10 mmol of D(−) ampicillin were converted into its trimethylsilyl ester and subsquently reacted with chlorosulfonyl isocyanate as in Example 7. A solution of 1.4 g (10 mmol) of ethyl glycinate hydrochloride and 3.5 ml (20 mmol) of triethylamine in about 50 ml of dry dichloromethane was added dropwise at −60° to −65°C and the manipulations thereafter were as usual. The desired product was extracted from water at pH 4.3 with a 1:1 mixture of diethyl ether and ethyl acetate and the combined extracts were washed with a small volume of ice-water, dried over anhydrous magnesium sulfate, concentrated to small volume, treated with a concentrated solution of sodium α-ethylcapronate etc to obtain 2.1 g (about 35%) of the colorless above named compound of about 95% purity.

IR (KBr-disc, values in cm$^{-1}$): ± 3500, ± 3330, ± 1765, 1740, 1680, 1610, ± 1520, 1220, 35 1325 and 1158.

PMR (d$_6$-DMSO, 60 Mc, γ-values in ppm, DSS as reference): 1.19 (t, J = 7.1 cps, 3H), 1.44 and 1.56 (6H), 3.71 (s, 21H), 4.05 (s) and 4.09 (q, J=7.1 cps) together 3H, about 5.4 (multiplet) and 3.58 (d, J≈7.5 cps) together 3H, about 7.35 (centre, about 6H), 9.0 (d, J≈7 cps, 0.8H).

EXAMPLE 11

Sodium D-6-[α-{3-(pyrid-3-ylaminosulfonyl)-ureido}-benzyl-carbonamido]-penicillanic acid 10 mmol of D(−) ampicillin were converted into its trimethylsilyl ester in the usual manner and then was reacted with chlorosulfonyl isocyanate as in Example 7. A solution of 3 g (32 mmol) of 3-aminopyridine in 15 ml of dichloromethane was added dropwise over the course of 10 minutes at −60°C and the reaction mixture was additionally stirred for 60 minutes aat −60°C and was subsequently poured into 100 ml of ice-water of pH 7.0. The layers were separated, the organic layer was discarded and the aqueous layer was extracted twice with dichloromethane and twice with diethyl ether. A solution of the desired penicillin was obtained by extraction of the remaining aqueous layer with a 1:1 mixture of ethyl acetate and diethyl ether at pH 4.5. This extract was washed with a small volume of ice-water, dried over anhydrous magnesium sulfate, filtered and concentrated in vacuo until a precipitate appeared. The precipitate was filtered using a suction pump, washed with cold diethyl ether and dried in vacuo to obtain 650 mg (about 10%) of the slightly colored above named acid slightly contaminated with diethyl ether and 3-aminopyridine.

IR (KBr-disc, values in cm$^{-1}$): ± 3350–3200, 3070,1780, ± 1705, 1692 and 1670, ± 1520, 1160.

PMR (d$_6$-DMSO and about 10 vol % DCO$_2$D, 60 Mc, γ-values in ppm, DSS as reference): 1.45 and 1.57 (6H), 4.27 (s, 1H), 5.45 (AB-q, J≈4.0 cps) and 5.55 (s) together 3H, centre at 7.3 and from about 7.1 to 7.8 (at least 7H), about 8.7 to 8.3 (about 2H).

In d$_6$-DMSO alone a doublet (J≈7.0 cps) at about 9.2 and another doublet at about 8.3 ppm.

EXAMPLE 12

Sodium D-6-[α-{3-(5-methylisoxazol-3-yl-aminosulfonyl)-ureido}-benzylcarbonamido]-penicillanate.

Starting with 10 mmol of D(−) ampicillin, the reaction was carried out in the same way as in Example 7. The introduced amount of 3-amino-5-methylisoxazole dissolved in dichloromethane was 35 mmol and the reaction mixture was treated in the usual way. The aqueous layer was repeatedly washed at pH 7.0 and the desired penicillin was obtained by extraction with a 1:1 mixture of ethyl acetate and diethyl ether at pH 4.3. The crude above named sodium salt weighed 2.7 g and it was stirred with dry acetone, vacuum filtered, washed with diethyl ether and dried in vacuo to obtain 2.2 g (about 35%) of the colorless sodium salt slightly contaminated with 3-amino-5-methylisoxazole.

IR (KBr-disc, values in cm$^{-1}$): ± 3500, 3350, 1770, ±0 1690–1670, ± 1615, ± 1510, 1165.

PMR (d$_6$-DMSO, 60 Mc, δ-values in ppm, DSS as reference): 1.44 and 1.56 (6H), 2.3 (narrow d), 4.13 (s, 1H), about 5.45 (multiplet) and 5.57 (d) together 3H, 6.0 (narrow q), about 7.35 (about 6H), 9.0 (d, J≈7. cps, 0.8H).

EXAMPLE 13

Sodium D-6-[α-{3-(3,4-dimethylisoxazol-5-yl-aminosulfonyl)-ureido}-benzylcarbonamido]-penicillanate Starting with 10 mmol of D(−) ampicillin, the reaction was carried out in the same way as in Example 7. The introduced amount of 3,4-dimethyl-5-aminoisoxazole dissolved in dichloromethane was 35 mmol and the reaction mixture was treated in the usual way. The aqueous layer was repeatedly washed at pH 7.0 and the desired penicillin was incompletely extracted at pH 4.5 with a 1:1 mixture of ethyl acetate and diethyl ether. The sodium salt of the above penicillanic acid product was prepared in the usual manner to obtain 1.15 g (about 19%) of an almost pure solid.

IR (KBr-disc, values in cm$^{-1}$): ± 3500, ± 3350, ± 3060, 1765, ± 1670, ± 1600 to ± 1620 (very intensive), 1495, ± 1520, ± 1320 and 1165.

PMR: (d$_6$-DMSO, 60 Mc, δ-values in ppm, DSS as reference): 1.45 and 1.58 (6H), 1.67 and 1.98 (singlets, 6H), 4.00 (s, 1H), about 5.4 (multiplet) and 5.62 (d, J≈8 cps) together 3H, about 7.35 (centre of multiplet) and 7.65 (d, J≈8 cps) together about 6H, 9.1 (d, J≈7 cps, 0.8H).

EXAMPLE 14

Sodium D-6-[α-{3-(morpholino-4-yl-sulfonyl)-ureido}-benzylcarbonamido]-penicillanate Employing anhydrous conditions, 2.45 ml (about 10 mmol) of N,O-bis(trimethylsilyl) acetamide were added to a suspension of 3.49 g (10 mmol) of D(−) ampicillin in 10 ml of dry dichloromethane. After 30 minutes stirring at room temperature, 20 ml of dry toluene were added and the reaction mixture was cooled to −65°C. A solution of 0.86 ml (10 mmol) of chlorosulfonyl isocyanate in 10 ml of toluene was introduced dropwise at −60° to −65°C, followed by 10 minutes additional stirring at −65° to −70°C. Subsequently, a solution of 2.7 ml (30 mmol) of morpholine in 10 ml of toluene was added dropwise at −65° ±5°C, followed by 60 minutes additional stirring at −65° to −70°C. The reaction mixture was poured into ice-water with a pH of 7.5 and the layers were separated. The organic layer was discarded and the aqueous layer was repeatedly extracted with dichloromethane and diethyl ether at pH 7.5. The washings were discarded and the aqueous layer at pH 6.0 to 4.5 was extracted a number of times with ethyl acetate. These extracts were combined, washed with a small volume of ice-water, dried over anhydrous magnesium sulfate, etc. to obtain 1.9 g (about 30%) of the almost colorless above named sodium salt somewhat contaminated with morpholine.

IR (KBr-disc, values in cm$^{-1}$): ± 3500, ± 3350, 3060,3035, 1775, ± 1680, 1610, ± 1515, ± 1320, 1160 and 1112.

PMR (d$_6$-DMSO, 60 Mc, δ-values in ppm, DSS as reference): 1.45 and 1.55 (6H), about 3.0 and about 3.6 (about 10H), 4.06 (s, 1H), about 5.4 and 5.56 (d) together 3H, about 7.35 and about 7.6 (unsharp d, together about 6H), 9.0 (d, 0.8H), 9.35 (broad s).

EXAMPLE 15

Sodium D-6-[α-{3-(ethoxycarbonylhydrazino-sulfonyl)-ureido}-benzylcarbonamido]-penicillanate Starting with 10 mmol of D(−) ampicillin, the reaction was carried out in the same way as in Example 7. After the addition of 35 mmol of ethoxycarbonylhydrazide, the solution was stirred for another 60 minutes at −65° to −70°C and then 2 ml of pyridine were added and the solution was poured into ice-water at pH 7. The layers were separated, the organic layer was discarded and the aqueous layer was repeatedly extracted a pH 7.0 with dichloromethane and thereafter with ethyl acetate to remove the excess of ethoxycarbonylhydrazide as completely as possible. Subsequently, the aqueous layer was extracted once with ethyl acetate at pH 4.7 and twice with a 1:1 mixture of ethyl acetate and diethyl ether at pH 3.8. These extracts were combined, washed with a small volume of ice-water, etc to obtain 2.23 g (37%) of the practically pure above named sodium salt.

IR (KBr-disc, values in cm$^{-1}$): ± 3200 – 3600 (very intensive), ± 1770, ± 1730, ± 1680, ± 1660, ± 1610, ± 1500-1560 (very intensive), 1170.

PMR (d$_6$-DMSO, 60 Mc, δ-values in ppm, DSS as reference): 1.17 (t, J=7.0 cps, 3H), 1.44 and 1.56 (6H), 4.06 (s) and 4.04 (q, J=7.0 cps) together 3H, about 5.4 and 5.6 (d) together 3H, about 7.35 and about 7 (broad) and about 7.5 together from about 6.8 to about 7.6 (about 7H), about 9.0 (d and s, 1.6H).

EXAMPLE 16

Sodium D-6-[α-{3-(aminosulfonyl)-ureido}-benzylcarbonamido]-penicillanate 10 mmol of D(−) ampicillin were successively reacted with equimolar amounts of N,O-bis(trimethylsilyl) acetamide and chlorosulfonyl isocyanate as in Example 7, followed by 10 minutes additional stirring at −60°C. 1.6 ml (20 mmol) of dry pyridine were added and the temperature was lowered to −70°C. Subsequently, 36 ml of a 0.277N solution of ammonia in diethyl ether were introduced at a fast rate causing a temperature rise to −45°C. The cooling bath was removed and the reaction mixture additionally stirred till it warmed up to 0°C. The mixture was poured into ice-water at pH 7.0. The layers were separated, the organic layer was discarded and the aqueous layer was repeatedly washed with diethyl ether at pH 7.0 and once with a 1:1 mixture of diethyl ether and ethyl acetate at pH 5.0. From the remaining aqueous layer, the desired product was incompletely removed by two extractions with a 3.1 mixture of ethyl acetate and diethyl ether at pH 3.8. These extracts were combined, washed with a small volume of ice-water, dried over anhydrous magnesium sulfate, filtered, concentrated to a small volume and treated with a concentrated solution of sodium α-ethylcapronate in ethyl acetate. The precipitated, almost colorless above named sodium salt was vacuum filtered, repeatedly washed with cold ethyl acetate and dried in vacuo to constant weight of 0.43 g (about 8%) with an estimated purity of 85–90%.

IR (KBr-disc, values in cm$^{-1}$): ± 3500, 3350–3400 (very intensive), 3060, 1765, 1665–1685, 1605, ± 1510, 1320 and 1155, 690.

PMR (d$_6$-DMSO, 60 Mc, δ-values in ppm, DSS as reference): 1.44 and 1.56 (6H), 4.00 and about 4.1* (together about 5H), 5.1* (somewhat broad s, about 0.4H), about 7.3 (about 5.5H), from about 5.25 to 5.7 (unresolved splitting pattern, 3H), about 9.0* (about 0.9H).

*All these absorption areas disappeared by addition of about 10 vol % of DCO$_2$D.

EXAMPLE 17

Disodium D-6-[α-{3-(sulfo)-ureido}-benzylcarbonamido]-penicillanate

Employing anhydrous conditions, 15.0 ml (about 60 mmol) of N,O-bis(trimethylsilyl) acetamide were added to a suspension of 21 g (60 mmol) of D(−) ampicillin in 100 ml of dry dichloromethane. After about 40 minutes additional stirring at room temperature, the solution was cooled to −65°C followed by the dropwise introduction over the course of about 10 minutes of a solution of 5.4 ml (about 64 mmol) of chlorosulfonyl isocyanate in 50 ml of dry dichloromethane at −65° to −70°C followed by 10 minutes additional stirring at the same temperature. Again at the same temperature, a solution of 30 ml of pyridine in 60 ml of dichloromethane was added and the stirring was continued for about 10 minutes. The cooling bath was replaced by a water bath and as soon as the temperature had risen to −5°C, the contents of the vessel were poured into 200 ml of well stirred ice-water. By adding dilute sodium hydroxide, the pH of the mixture was adjusted to 7.0 and the two layer system was vigorously stirred at 0°C for 90 minutes whereby the pH decreased not more than 0.5 unit. The pH was readjusted to 7.0 and the layers were separated. The organic layer was discarded and the aqueous layer was repeatedly washed with dichloromethane. Subsequently, the aqueous layer was acidified to pH 30 and was extracted a few times with ethyl acetate. These extracts were combined, washed with a small volume of ice-water, dried over anhydrous magnesium sulfate, filtered, concentrated in vacuo in the cold to a small volume and treated with a concentrated solution of sodiumm α-ethylcapronate. The obtained precipitate was vacuum filtered, washed with cold ethyl acetate and cold acetone and dried in vacuo to constant weight to obtain 7.0 g (20%) of the above named disodium salt which contained approximately 2 moles of water and was virtually pure.

IR (KBr-disc, values in cm$^{-1}$): about 3200–3600 (very intensive) 1770, ± 1670, ± 1685, ± 1605, ± 1530, 1495, 1330 and 1170.

PMR (d$_6$-DMSO, 60 Mc, δ-values in ppm, DSS as reference): 1.44 and 1.55 (6H), 3.95 (s, 1H), about 5.2 to 5.7 (unresolved splitting pattern, 3H), about 7.3 (5H), NH absorptions at 5.0 (possibly, somewhat broad s, about 0.4H), at 6.4 (probably, broad, about 0.5H), and at about 9.0 (broad, 0.8H).

After addition of about 10 vol % of DCO$_2$D, all NH absorptions disappeared.

EXAMPLE 18

Sodium D-6-[α-(aminosulfonylamino)-benzylcarbomido]-penicillanate

A suspension of 3.5 g (10 mmol) of D(−) ampicillin in 50 ml of dry dichloromethane was reacted with 2.5 ml of N,O-bis(trimethylsilyl) acetamide followed by 30 minutes additional stirring at room temperature. The resulting solution was cooled to 3°C whereupon 1 ml (about 12mmol) of dry pyridine was added followed by the dropwise introduction of a solution of 1.25 g (10 mmol) of aminosulfonyl chloride (H$_2$N—SO$_2$—Cl), prepared from chlorosulfonyl isocyanate and formic acid according to Appel et al. [Chem. Ber. 91, (1958) 1339] in 20 ml of dry dichloromethane. During the addition, the temperature was between 3° and 5°C and at the same temperature, the solution was additionally stirred for 60 minutes. The reaction mixture was poured into ice-water of pH 7.0, etc. The desired penicillin was extracted from the aqueous layer at pH 4.0 with a 1:1 mixture of ethyl acetate and diethyl ether to obtain 1.0 g (21%) of the almost pure above named sodium salt.

IR (KBr-disc, values in cm$^{-1}$): ± 3550, about 3380–3200 (intensive), 3060, 1765, 1680, 1605, ± 1550, ± 1500, ± 1315, 1157, 735 and 690.

PMR (d$_6$-DMSO, 60 Mc, δ-values in ppm, DSS as reference): 1.44 and 1.55 (6H), about 3.6, 3.93 (1H), about 5.4 and 5.22 (s) together 3H, about 6.7 (centre of broad absorption), about 7.35 (5H), 8.85 (d, about 0.8H).

EXAMPLE 19

Sodium D-6-[α-(ethoxycarbonylaminosulfonylamino)-benzylcarbonamido]-penicillanate A suspension of 3.5 g (10 mmol) of D(−) ampicillin in 50 ml of dry dichloromethane was reacted with 2.5 ml of N,O-bis(trimethylsilyl) acetamide followed by 30 minutes of additional stirring at room temperature. The resulting solution was cooled to 5°C whereupon 5 ml of dry pyridine were added followed by the dropwise introduction of a solution of 2g (about 11.5 mmol) of ethoxycarbonylaminosulfonyl chloride (C$_2$H$_5$OCONH-SO$_2$Cl, prepared from chlorosulfonyl isocyanate and ethanol according to Graf, German Patent No. 931,467) in 20 ml of dichloromethane at 5°C. The reaction mixture was additionally stirred for 60 minutes at 5°C and subsequently 90 minutes at room temperature. The reaction mixture was treated as usual. The desired penicillin was extracted at pH 4.0 with diethyl ether, and converted into its sodium salt obtain 0.65 g (about 12%) in the form of a colorless solid of about 90% purity.

IR (KBr-disc, values in cm$^{-1}$): ± 3500, about 3200 to about 3400, 1770, 1670, 1610, 1540, ± 1270, 1155.

PMR (d$_6$-DMSCO, 60 Mc, δ-values in ppm, DSS as reference): 1.45 and 1.57 (6H), 1.08 (t, J=7.0 cps, 3H), 3.84, (q, J=7.0 cps) and 4.09 (s) together 3H, 5.28 (slightly broad s) and about 5.4, together 3H, about 6.6 (broad, about 0.7H), 7.35 (5H), about 8.9 (d, about 0.7H).

EXAMPLE 20

Sodium D-6-[α-(phenoxycarbonylaminosulfonylamino)-benzylcarbonamido]-penicillanate Starting with 10 mmol of D(−) ampicillin, the reactions were carried out in the same way as in Example 19, but with 10.6 mmol of phenoxycarbonylaminosulfonyl chloride while the addition of pyridine was omitted. The desired penicillin was extracted at pH 4.0 with ethyl acetate to obtain 1.62 g (about 26%) of the slightly colored above named sodium salt of 85–90% purity.

IR (KBr-disc, values in cm$^{-1}$): ± 3500, about 3200 to about 3400, 1770, ± 1660 – 1685, 1610, ± 1525 and ± 1545, ± 1300, 1150, 1220.

PMR (d$_6$-DMSO, 60 Mc, δ-values in ppm, DSS as reference): 1.47 and 1.57 (6H), 3.96 (s,1H), 5.22 (slightly broad s) and about 5.4 together 3H, about 6.6 to 7.65 (extended multiplets, about 10H), low broad absorptions at about 6.3 and 8.6.

EXAMPLE 21

Sodium D-6-[α-{(1-dimethylamino)-ethylideneamino-sulfonamido} benzylcarbonamido]-penicillanate 2.5 ml of N,O-bis(trimethylsilyl) acetamide were added to a suspension of 3.5 g (10 mmol) of D(−) ampicillin in 15 ml of dichloromethane and the mixture was stirred at room temperature until a clear solution was obtained. 9.8 ml of dry pyridine were added and the solution was cooled to about 3°C with an ice-bath. A solution of 1.84 g (about 10 mmol) of N,N-dimethyl-N'-chlorosulfonylacetamidine (CH$_3$)$_2$N—C(CH$_3$)=N—SO$_2$Cl, prepared from chlorosulfonyl isocyanate and N,N-dimethyl acetamide according to Graf et al. [Deutsches Auslegeschrift No. 1,144,718 (1963)] in 10 ml of dichloromethane was added dropwise at 0°–5°C. The resulting reaction was additionally stirred for 60 minutes at about 0°C and thereafter 60 minutes at room temperature. The reaction mixture was poured into ice-water at pH 7.0 and the layers were separated. The organic layer was discarded and the aqueous layer was twice washed at pH 7.0 with diethyl ether and the remaining aqueous layer was acidified to pH 3.5 and extracted once with a 1:1 mixture of diethyl ether and ethyl acetate. Incomplete removal of the desired product necessitated further extraction of the aqueous layer at pH 2.5 with the mixture of ethyl acetate and diethyl ether (once) and with ethyl acetate (3 times). The five extracts were combined, washed with cold water saturated with sodium chloride, dried over anhydrous magnesium sulfate, treated with activated carbon, etc. The resulting almost colorless solution was concentrated to some extent in vacuo and treated with sodium α-ethylcapronate in the usual manner to obtain 3.0 g (55%) of the above named sodium salt in the form of a colorless, practically pure solid.

IR (KBr-disc, values in cm$^{-1}$): ± 3550, ± 3300, 1770, 1675, 1605, 1570, ± 1505, 1495, 1130.

PMR (d$_6$-DMSO, 60 Mc, δ-values in ppm, DSS as reference): 1.44 and 1.56 (6H), 2.33 (s, 3H), 2.87 and 3.02 (δν= 9.2 cps, 6H), 3.93 (s, 1H) about 5.4 (multiplet, J$_{5,6}$≈4.0 cps) and 5.22 (d, J≈9.5 cps) together 3H, about 7.4 (multiplet) and 7.05 (d, J≈9.7 cps) together about 6H, 8.9 (d, J≈7.5 cps, about 0.9H).

EXAMPLE 22

Sodium D-6-[α-{3-(bis-ethylmercapto-phosphinyl)-ureido}-benzylcarbonamido]-penicillanic acid Employing anhydrous conditions, a solution of 2.0 g (about 20 mmol) of phosgene in 30 ml of toluene was cooled to −70°C followed by simultaneous and dropwise additions of a solution of 4 g of pyridine in 25 ml of dry toluene and of a solution of 3.7 g (20 mmol) of bis-ethylmercapto-phosphinyl amide [(C$_2$H$_5$S)$_2$P(O)NH$_2$] in 30 ml of dry dichloromethane at about −70°C. After completion of the simultaneous additions, the internal temperature of the reaction mixture was gradually and slowly raised to about −10°C whereupon the flask was placed in an ice-water bath and the stirring was continued for 90 minutes. The resulting solution, containing crude bis-ethylmercapto-phosphinyl isocyanate (C$_2$H$_5$S)$_2$P(O)NCO, was concentrated in vacuo to a volume of about 35 ml, and thereafter dry toluene was added to give a volume of about 50 ml. This solution was added dropwise at 10°C to a solution prepared as usual from 3.5 g (10 mmol) of D(−) ampicillin, 2.5 ml of N,O-bis(trimethylsilyl) acetamide and 25 ml of dry dichloromethane. The resulting reaction mixture was additionally stirred for 30 minutes at 10°C and subsequently was poured at pH 7.0 into a well stirred mixture of ethyl acetate and an ice-cold saturated solution of sodium chloride in water. The layers were separated, the organic layer was discarded, and the aqueous layer was repeatedly washed with ethyl acetate at pH 7.0. From the remaining aqueous layer, the desired product was completely and selectively removed by a number of consecutive extractions: diethyl ether at pH 4.5, a 9:1 mixture of diethyl ether and ethyl acetate at pH 4.0, a 1:1 mixture of the same solvents at pH 3.7, and finally ethyl acetate alone at pH 3.5. These extracts were combined, washed with a cold saturated solution of sodium chloride in water, dried over anhydrous magnesium sulfate, vacuum filtered, concentrated in vacuo to about 15 ml and diethyl ether was added with shaking until a precipitate appeared. This precipitate was vacuum filtered, washed with cold diethyl ether and dried in vacuo to obtain 1.5 g (26.5%) of the pure and colorless above named acid. The filtrate and the washings were combined and in the usual manner treated with sodium α-ethylcapronate and the obtained sodium salt of the desired penicillin weighed 1.2 g (about 20 %).

IR (KBr-disc, values in cm$^{-1}$): ± 3500, ± 2600, ± 3220, ± 3270 to 3340, ± 1780, about 1650 to 1720 (very intensive absorption area), ± 1520 (very intensive), 1455, 1375, 1305, 1270, 1160 - 1235, 1135, 1050, 900, 740 and 700. PMR (d$_6$-DMSO, 60 Mc, δ-values in ppm, DSS as reference): 1.3 (2 almost coinciding t, J=7.2 cps), 1.42 and 1.56 together 12H, from about 2.45 to 3.3 (extensive multiplets, 4H), 4.21 (s, 1H), about 5.45 (multiplet, J$_{5,6}$≈4.0 cps) and 5.25 (d) together 3H, about 7.3 and 7.5 (d) together about 6H, 9.15 (d, about 0.8H).

EXAMPLE 23

Sodium D-6-[α-{(1-methyl)-pyrrolidin-2-yl-ideneamino-sulfonamido}-benzylcarbonamido]-penicillanate A solution prepared in the usual manner from 7 g (20 mmol) of D(−) ampicillin, 4.8 ml of N,O-bis-(trimethylsilyl) acetamide and 20 ml of dichloromethane at 0°C was added dropwise to a red solution of 3.8 g (19.4 mmol) of 1-methyl-2-chlorosulfonylimino-pyrrolidine [prepared from 1-methylpyrrolidone (20 mmol) and chlorosulfonyl isocyanate (20 mmol)] in a mixture of 20 ml of pyridine and 20 ml of dichloromethane. During the addition, the color became deeper. After completion of the addition, the reaction mixture was additionally stirred for 30 minutes at 0°C and 60 minutes at room temperature. The mixture was poured into ice-water at pH 7.0 and the layers were separated. The organic layer was discarded and the aqueous layer was repeatedly washed with diethyl ether. The remaining aqueous layer was extracted 10 times with ethyl acetate at pH 3.6 and the combined extracts were washed once with a small volume of a saturated sodium chloride solution, treated with activated charcoal, dried over anhydrous magnesium sulfate, filtered and concentrated in vacuo to a volume of about 100 ml. A concentrated solution of sodium α-ethylcapronate was added and the resulting solid precipitate was collected by filtration, washed with cold ethyl acetate and dried in vacuo to obtain 9.09 g (about 73%) of the colorless above named sodium salt which contained about 1 mole of ethyl acetate per mole of penicillin. IR (KBr-disc, values in $cm^{-1}$): about 3200 – 3600, 1770, 1675, ± 1600 (very intensive), ± 1530, 1495, ± 1320 and 1150.

PMR ($d_6$-DMSO, 60 Mc, δ-values in ppm, DSS as reference): 1.43 and 1.57 (6H), from about 1.75 to 2.2 (multiplet, 2H), 2.76 (s) and about 2.9 (centre) together 5H, 3.4 (centre, 2H), 4.23 (s, 1H), ± 5.35 (multiplet, $J_{5,6}$≈4.0 cps) and 5.17 (d, J≈10 cps) together 3H, 7.07 (d, J≈10 cps) and 7.3 (centre of multiplet) together about 6H, 8.95 (d, J≈7.0 cps, 0.9H).

EXAMPLE 24

Sodium
D-6-[α-{3-(dianilino-phosphinyl)-ureido}-benzylcarbonamido]-penicillanate A solution prepared as usual from 4.4 g (12.5 mmol) of D(−) ampicillin, 2.9 ml of N,O-bis(trimethylsilyl) acetamide and 15 ml of dry dichloromethane was added dropwise to a solution of 2.0 g (12.5 mmol) of redistilled dichlorophosphinyl isocyanate ($Cl_2P(O)NCO$) in 15 ml of dry dichloromethane at −70°C over the course of 30 minutes. The resulting solution was additionally stirred at the same temperature for 10 minutes followed by the dropwise introduction over the course of 10 minutes of a solution of 4.6 ml (about 50 mmol) of aniline in 5 ml of dichloromethane. The resulting solution was stirred for 60 minutes at −70°C, another 39 minutes at temperatures gradually rising from −70°C to room temperature and finally 1 hour at room temperature. The reaction mixture was poured into ice-water at pH 7.0 which caused a precipitate and acetone was added until a clear two-layer system was obtained followed by the removal of low-boiling solvents in vacuo. Diethyl ether was added and the resulting layers were separated at pH 7.0. The organic layer was discarded and the aqueous layer was repeatedly washed with diethyl ether. The aqueous layer was washed once more at pH 6.0 with ethyl acetate which resulted in the loss of part of the desired compound. Extraction at pH 4.3 with ethyl acetate resulted in incomplete removal of the desired compound. This extract was washed twice with ice-water buffered to pH 4.6 and once with ice-water. The virtually clear extract obtained in this manner was used to obtain the above named sodium salt of the desired penicillin in the usual manner. The yield was 0.45 g (about 5%) of a slightly colored solid somewhat contaminated with sodium α-ethylcapronate.

IR (KBr-disc, values in $cm^{-1}$): ± 3100 – 3600 (very intensive absorption), 1765, about 1660 – 1680, ± 1605, about 1530 – 1560, ± 1505, 1415 (intensive), 1330, ± 1300, 1240, 960 – 980, 945, ± 760 and ± 705.

PMR ($d_6$-DMSO containing about 5 vol % $DCO_2D$, 60 Mc, δ-values in ppm, DSS as reference): 1.45 and 1.57 (6H), 4.25 (s, 1H), 5.45 (centre of AB-q, $J_{5,6}$≈4.0 cps) and 5.65 together 3H, 7.35 (centre) and extended multiplet together from about 6.7 to 7.65 (about 15H).

EXAMPLE 25

Sodium
D-6-[α-{3-(anilinoethoxyphosphinyl)-ureido}-benzylcarbonamido]-penicillanate A solution prepared in the usual manner from 1.43 g (4.1 mmol) of D(−) ampicillin, 1.0 ml of N,O-bis(trimethylsilyl) acetamide and 25 ml of dry dichloromethane was added dropwise to a solution of 0.7 g (4.1 mmol) of redistilled chloro(ethoxy)phosphinyl isocyanate [$C_2H_5O-P(O)(Cl)NCO$, prepared according to A. V. Narbut and G.I. Derkach, Zh. obsl ch. Khim. 38, 1312 (1968)] in 10 ml of dichloromethane at −65° to −70°C over the course of 30 minutes. The solution was additionally stirred for 15 minutes at about −65°C followed by the addition of a solution of 0.76 ml (about 8.3 mmol) of aniline in 10 ml of dichloromethane at −60° to −70°C. The addition was completed in 5 minutes, and the solution was additionally stirred for 1 hour at −60°C, 30 minutes at −40°C and finally 1 hour at 0°C. The reaction mixture was poured into ice-water at pH 7.0 and thereafter dichloromethane was removed in vacuo followed by the addition of diethyl ether until a clear two-layer system was obtained. The layers were separated, the organic layer was discarded and the aqueous layer at pH 7.0 was repeatedly washed with diethyl ether. To achieve selective extraction of the desired product, the remaining aqueous layer was repeatedly extracted at pH 4.7 – 4.8 with ethyl acetate. These extracts were combined, washed once with a small volume of ice-water saturated with sodium chloride, dried over anhydrous magnesium sulfate, filtered, concentrated in vacuo and treated with a concentrated solution of sodium α-ethylcapronate in ethyl acetate, followed by addition of diethyl ether. The almost colorless precipitate was vacuum filtered, washed with diethyl ether and dried in vacuo to obtain 0.7 g (25%) of the colorless, practically pure above named sodium salt.

IR (KBr-disc, values in $cm^{-1}$): ± 3550, 3200 – 3400, 1770, ± 1670, 1600, ± 1515, 1495, ± 1215, 1030.

PMR ($d_6$-DMSO, 60 Mc, δ-values in ppm, DSS as reference): 1.25 (centre of 2 unequally intensive triplets, (δν= 2.2 cps), J≈7.0 cps) and 1.44 and 1.56 together 9H, 4.08 (s) and about 3.8 to 4.35 (multiplet) together 3H, about 5.4 (centre of multiplet, $J_{5,6}$≈4.0 cps) and 5.60 (d, J≈8 cps) together 3H, 7.35 (centre) and extended multiplet, together from about 6.65 to 7.55 (10H), 7.8 (probably 2 close d, J≈8–8.5 cps), 8.0 )J≈8.5 –9 cps), about 8.65 (broad), 9.1 (d, J≈7.0 cps).

EXAMPLE 26

Sodium
D-6-[α-{3-(ethoxy-hydroxy-phosphinyl)-ureido}-benzylcarbonamido]-penicillanic acid A solution prepared in the usual manner from 4.7 g (13.5 mmol) of D(−) ampicillin, 3.3 ml of N,O-bis-(trimethylsilyl) acetamide and 20 ml of dichloromethane was added at −65° to −70°C to a solution of 2.3 g (13.5 mmol) of chloro(ethoxy) phosphinyl isocyanate [$C_2H_5O-P(O)(Cl)NCO$] in 20 ml of dichloromethane. After completion of the addition, stirring was continued for 20 minutes at −65°C and then the reaction mixture was poured slowly into ice-water while simultaneously dilute sodium hydroxide was added to maintain the pH at 7.0. Stirring and addition of base was continued until no further change of pH took place. The layers were separated, the organic layer was discarded and the aqueous layer was washed with ethyl acetate once at pH 7.0 and once at pH 4.5. These washings too were discarded and the remaining aqueous layer was extracted three times at pH 1.5 with an excess volume of ethyl acetate. These extracts were combined, quickly dried over anhydrous magnesium sulfate and immediately filtered since a precipitate appeared in the filtrate rather soon. The turbid filtrate was completely evaporated in vacuo and after extensive drying in vacuo, the residual, almost colorless above named sodium salt weighed 0.4 g (about 5.5%). The product was at least 90% pure.

IR (KBr-disc, values in cm$^{-1}$): ± 3550, ± 2600, ± 3320 and ± 3250, 1780, 1740 − 1710, 1640 − 1670, ± 1530 (intensive), 1210, 1040, 700.

PMR (d$_6$-DMSO, 60 Mc, δ-values in ppm, DSS as reference): 1.2 (t, J = 7.0 cps, 3H), 1.44 and 1.58 (6H), 3.95 (multiplet) and 4.24 (s) together 3H, about 5.5 (multiplet, J$_{5,6}$ = 4.0 cps) and about 5.65 (d) together 3H, about 7.4 (5H), 7.7 (d, J≈8.5 cps), 7.9 (d, J≈7.5 cps), 9.15 (d, J≈7.5 cps).

EXAMPLE 27

D-7-[α-{3-(diethoxyphosphinyl)-ureido}-benzylcarbonamido]desacetoxycephalosporanic acid Employing anhydrous conditions, 0.63 ml (about 2.7 mmol) of N,O-bis(trimethylsilyl) acetamide were added to a suspension of 0.8 g (2.3 mmol) of D(−) 7-α-aminobenzylcarbonamido-desacetoxycephalosporanic acid (cephalexin) in 20 ml of dichloromethane. A clear solution was obtained by stirring the mixture for 2.5 hours at 30°C and then a solution of 0.4 g (2.3 mmol) of redistilled diethoxy phosphinyl isocyanate [$(C_2H_5O)_2P(O)NCO$] in 10 ml of dichloromethane was added at 0°–5°C. After completion of the dropwise addition, the ice-bath was removed and the reaction mixture was additionally stirred for about 10 minutes. The reaction mixture was then poured into a well stirred mixture of ice-water and ethyl acetate, resulting in the formation of a solid precipitate. The pH of the mixture was adjusted to about 3.8, whereupon the mixture was concentrated in vacuo in order to remove organic solvents. Subsequently, the precipitate was recovered by vacuum filtration, washed with water and diethyl ether and dried to constant weight in vacuo to obtain 1.1 g (90%) of the colorless, pure above named acid.

IR (KBr-disc, values in cm$^{-1}$): 3420, 3270, ± 2250, 1780, ± 1705, ± 1680 (sh), ± 1640, 1595, 1495, ± 1550, 1440, 1230 and ± 1040.

PMR (d$_6$-DMSO, 60 Mc, δ-values in ppm, DSS as reference): 1.25 (centre of 2 close triplets, δν = 1.5 cps, J = 7.1 cps, 6H), 2.01 (s, 3H), from about 3.75 to 4.3 (2 multiplets, 4H), 3.37 (AB-q, J$_{AB}$≈ 18 cps, 2H), 4.95 (d, J = 4.7 cps, 1H) 5.53 (d) and 5.63 (q) together 2H, 7.35 and 7.52 (d, J≈7.8 cps) together about 6H, 8.25 (d, J≈8.7 cps, about 1H), 9.3 (d, J≈7.8 cps, about 1H).

Using the same procedure, 3.17 mmol of redistilled diethoxyphosphinothioyl isocyanate [$(C_2H_5O)_2P(S)NCO$] was reacted under identical reaction conditions to obtain a quantitative yield of sodium D-7-[α-{3-(diethoxyphosphinothioyl)-ureido}-benzylcarbonamido]-desacetoxycephalosporanate. Isolation of product by extraction from water at pH 3.0 with ethyl acetate, etc. followed by addition of sodium α-ethylcapronate resulted in 1.3 g (72%) of the sodium salt.

IR (ibidem): From about 3200 to 3600, 1760, ± 1660 to 1690, ± 1600, ± 1540, 1415, 1365, 1035, 980, 830 and 800.

PMR (ibidem): 1.2 (centre of 2 close triplets, δν 1.8 cps, J = 7.1 cps, 6H), 1.95 (s, 3H), 3.2 (centre of AB-q, J≈17.5 cps, 2H), 3.6 to 4.3 (2 multiplets, 4H), 4.85 (d, J = 4.6 cps, 1H), 5.5 (centre of multiplet, 2H), about 7.35 (about 6H), 7.7 (d, J≈8 cps, about 1H), 9.2 (d, J≈8 cps, about 1H).

Using the same procedure, 2.7 mmol of redistilled diphenoxyphosphinyl isocyanate [$(C_6H_5O)_2P(O)NCO$] was reacted. The solution of the isocyanate in dichloromethane was added at 0°C within 5 minutes. Immediately thereafter, the icebath was removed and the solution was additionally stirred during about 40 minutes. The reaction mixture was poured into iced water of pH 7.0 and the mixture was acidified in the cold to pH 2.5. Sodium chloride and acetone were added until a clear two-layer system was reached. The layers were separated, the water-layer was saturated with sodium chloride and again extracted with acetone. The organic extracts were combined whereupon the volume was doubled by adding ethyl acetate. The solution was concentrated in vacuo until the lower boiling solvents were virtually removed. The remaining solution was dried over anhydrous magnesium sulfate and filtered on a vaccum filter. A concentrated solution of about 2.6 mmol of sodium α-ethyl-capronate was added followed by the addition of dry diethyl ether. The precipitated salt was collected by filtration, was washed with cold diethyl ether and dried in vacuo to obtain 1.5 g (about 85%) of sodium D-7-[α-{3-(diphenoxyphosphinyl)-ureido}-benzylcarbonamido]-desacetoxycephalosporanate which appeared to be virtually pure according to thin-layer chromatograms, IR and PMR spectra.

IR (ibidem): ± 3500, 3260, 3060, 1760, ± 1680 (sh), 1650, ± 1590, 1545, 1490, 1450, 1410, 1365, 1250, 1220, 1200, 1185, 1075, 1050, 1030, 1010, 950–980, 910 (sh), 770, 755 (sh) PMR (ibidem): 1.95 (s, 3H); 3.2 (centre of AB-q, J≈18 cps, 2H); 4.85 (d, J≈4.6 cps, 1H); 5.55 (centre of multiplet, 2H); about 6.7 to 8.1 (multiplet, 16-17H); 9.25 (d, J≈8 cps, about 0.9H).

EXAMPLE 28

Sodium D-6-[α-{3-(ethoxycarbonylhydrazino-ethoxy-phosphinyl)-ureido}-benzylcarbonamido]-penicillanate A solution prepared in the usual manner from 3.9 g (11 mmol) of D(−) ampicillin, 2.5 ml of N,O-bis-(trimethylsilyl) acetamide and 20 ml of dichloromethane was added dropwise at about −70°C over the course of 15 minutes to a solution of 1.88 g (11 mmol) of redistilled chloro(ethoxy) phosphinyl isocyanate [$C_2H_5O-P(O)(Cl)NCO$] in 25 ml of dichloromethane. The solution was stirred for another 15 minutes at about −70°C and then 2 ml of pyridine and (again at about −70°C) a solution of 1.2 g (11 mmol) of ethoxycarbonylhydrazide in 10 ml of dichloromethane were added. The resulting solution was kept at about −60°C for 2 hours and subsequently was poured into icewater. The pH was adjusted to 7.0 and the two-layer system was concentrated in vacuo in order to remove dichloromethane. The remaining aqueous layer was repeatedly extracted at pH 7.0 with ethyl acetate in order to remove unreacted ethoxycarbonylhydrazide and a by-product. The remaining aqueous layer (about 100 ml) was saturated with sodium chloride, acidified to pH 3.0 and extracted 8 times with 70 ml volumes of ethyl acetate at the same pH. These extracts were combined, washed twice with a small volume of ice-water saturated with sodium chloride, once with ice-water at pH 1.0 and once with ice-water. The resulting organic solution was dried over anhydrous magnesium sulfate, vacuum filtered and the filtrate was concentrated in vacuo to small volume. The concentrated solution was treated in the usual manner with a concentrated solution of sodium α-ethylcapronate in ethyl acetate, etc to obtain 1.1 g (15%) of the colorless, almost pure above named sodium salt.

IR (KBr-disc, values in cm$^{-1}$): ± 3280 (broad and intensive), 1765, ± 1720, ± 1680, ± 1650, 1610, ± 1500–1530, 1195, 1030.

PMR (mixture of d$_6$-DMSO and about 5% DCO$_2$D, 60 Mc,δ-values in ppm, DSS as reference): 1.18 (t) and about 1.27 (centre of 2 close triplets) and 1.45 and 1.58, together about 12H, from about 3.85 to 4.4 (multiplets) and 4.25 (s) together 5H, 5.47 (AB-q, J = 4.1 cps) and 5.60 (s) together 3H, about 7.4 (about 5H). The spectrum in d$_6$-DMSO alone revealed signals at 7.95 (d), 8.7 (broad s, possibly 2H) and 8.9 (d), while one signal was probably hidden at about 7.4.

EXAMPLE 29

Sodium D-6-[α-{(ethoxy) (N'-phenylureido)-phosphinylamido}-benzylcarbonamido]-penicillanate Following the description given by Narbut et al. [Derkach, Zh, Obshch. Khim., 38 (1968), 1321], a solution of 1.7 g (10 mmol) of chloro(ethoxy)phosphinyl isocyanate [$C_2H_5OP(O)(Cl)NCO$] in 20 ml of dry diethyl ether was added dropwise at 0°–5°C to a solution of 0.93 g (10 mmol) of aniline in 25 ml of dry diethyl ether. A brownish oil precipitated and solvent was removed. The residue, crude ethoxy(phenylureido)phosphinyl chloride [$C_6H_5NH-CO-NH-P(O)(Cl)OC_2H_5$] was dissolved in 35 ml of dry dichloromethane and this solution was added dropwise at 5°–10°C to a solution prepared in the usual manner from 3.5 g (10 mmol) of D(−) ampicillin, 2.5 ml of N,O-bis(trimethylsilyl)-acetamide and 15 ml of dry dichloromethane to which 1 ml of pyridine was added after its preparation. After completion of the addition, the ice-bath was removed and stirring was continued for 2 hours at room temperature. The reaction mixture was then poured into icewater, the pH was adjusted to 7.0, diethyl ether and sodium chloride were added and the resulting layers were separated. The upper organic layer was discarded and the aqueous layer was purified by extractions with diethyl ether at pH 7.0 and 6.0. A solution of the desired penicillin was obtained by extraction of the aqueous layer at pH 4.5 with ethyl acetate. This solution was washed with a small volume of ice-water, dried over anhydrous magnesium sulfate, etc to obtain the above named sodium salt prepared in the usual manner as a yield of 2.0 g (about 30%) of an almost colorless solid.

IR (KBr-disc, values in cm$^{-1}$): about 3250 (broad and intensive), 1770, about 1680, ± 1605 (very intensive), ± 1550, 1500, 1460, 1400, 1325, ± 1230 (broad), 1040, 765 and 700.

PMR (d$_6$-DMSO containing about 5% of DCO$_2$D, 60 Mc, δ-values in ppm, DSS as reference): 1.2 (sharp triplet, J = 7.1 cps, 3H), 1.45 and 1.56 (6H), 4.0 (centre of multiplet) and 4.25 (s), together 3H, 5.2 (d, J$_{P-H}$ = 10.5 cps) and 5.45 (AB-q, J$_{AB}$ = 4.2 cps) together about 3H, from about 7.1 to 7.7 (10H). The spectrum in DMSO alone revealed signals at 8.9 (possibly d), 9.3 (low broad) and about 10.15 (possibly d) while the initial signal at 1.2 appeared as 2 triplets ( (δν≈± 3 cps).

EXAMPLE 30

D-7-[α-{3-hydroxy(ethoxy)phosphinyl)-ureido}-benzylcarbonamido]-desacetoxycephalosporanic acid By reaction with about 7 mmol of N,O-bis(trimethylsilyl) acetamide, a solution of 2.1 g (6 mmol) of cephalexin in 20 ml of dichloromethane was prepared in the usual manner. Substantially following the method of Example 26, this solution was added over 30 minutes to a solution of 1.0 g (6mmol) of chloro(ethoxy)-phosphinyl isocyanate in 15 ml of dichloromethane and during the addition, the reaction temperature was kept below −70°C. After 60 minutes additional stirring at −70°C, the reaction mixture was gradually warmed up to 0°C and subsequently was poured into crushed ice. The pH was increased to 4.0 and the resulting emulsion was clarified by the addition of an excess volume of ethyl acetate whereupon the layers were separated. The organic layer was discarded, ethyl acetate was mixed with water-layer and the pH lowered to 1.5. A solid precipitate was formed which was collected by filtration, was washed with ethyl acetate and dried in vacuo over phosphorus pentoxide to obtain 0.75 g (25%) of about 90% pure above named acid. The two layers of the filtrate were separated, the organic layer was discarded and the water-layer was concentrated in vacuo. The precipitated solid was separated by filtration and was washed with ethyl acetate. After drying, the second crop weighed 1.1g (36%). Thin-layer chromatograms and IR spectra of both crops were indistinguishable for a total yield of 1.85 g (61%).

IR (KBr-disc, values in cm$^{-1}$): ± 3550 and ± 2500, 3270, 1770, ± 1710 (sh), 1640 (very intensive with shoulders at about 1660 and 1680), 1545, 1450, ± 1370, 1320, 1220–1260, 1190, 1165, ± 1075, (sh), 1050, 970 and 700. PMR (about 7:1 mixture of d$_6$-

DMSO and DCO$_2$D, 60 Mc, DSS, δ-values in cm$^{-1}$): 1.2 (triplet-like, J≈7.0 cps, 3H); 2.0 (s, 3H); about 3.35 (centre of incompletely resolved AB-q, 2H); about 4.0 (centre of complex multiplet, 2H); 4.95 (d, J≈4.6 cps, 1H); about 5.55 (broadened s) and 5.65 (d, J≈4.6 cps) together 2H; 7.35 (5H).

Starting from 1.8 g (5 mmol) of cephalexin and 1.0 g (5 mmol) of chloro(isobutoxy) phosphinyl isocyanate [i-C$_4$H$_9$O—P(O)(Cl)NCO], 1.5 g (about 55%) of D-7-[α-{3-hydroxy(isobutoxy) phosphinyl ureido}-benzyl-carbonamido]-desacetoxycephalosporanic acid of about 90% purity was obtained.

IR (ibidem): ± 3500 and ± 2600, 3270, 3060, 2960, 1770, ± 1710 (sh), 1640 (very intensive with shoulders at about 1660 and 1680), 1550, ± 1470, ± 1440, 1370, 1330, ± 1240, ± 1190, ± 1080 (sh), 1050 and 700.

PMR (about 5:1 mixture of d$_6$-DMSO and DCO$_2$D, 60 Mc, DSS, δ-values in ppm): 0.86 (d, J α 6.5 cps, 6H); 2.03 (s, 3H); about 1.7 (multiplet, about 1H); about 3.35 and about 3.65 (multiplet) together 4H; 4.95 (d, J≈4.6 cps, 1H); about 5.55 (narrow doublet) and about 5.65 (d, J≈4.6 cps) together 2H; about 7.35 (5H). In the spectrum of a solution in d$_6$-DMSO alone, NH-absorptions appeared at about 6.0 (d) and at about 9.25 (d, J≈8.5 cps).

EXAMPLE 31

Pivaloyloxymethyl esters of N-substituted D(−) ampicillins

T-butylcarbonyloxymethyl esters, otherwise named pivaloyloxymethyl esters, of several N-substituted ampicillins prepared in proceeding examples, were obtained employing two different methods. In one method, the desired compounds were obtained by reaction of Pivampicillin (short name for the hydrochloric acid salt of the t-butylcarbonyloxymethyl ester of D(−) α-amino-benzylpenicillin) with the corresponding isocyanates (Method I) and in the other method, the desired esters were obtained by reaction of salts of N-substituted ampicillins with t-butylcarbonyloxymethyl chloride (Method II).

Method I

Pivaloyloxymethyl D-6 [α-{3-(diphenoxyphosphinyl)-ureido}-benzylcarbonamido]-penicillanate (ester of compound of Example 2)

Under anhydrous conditions, 0.5 ml of triethylamine dissolved in 10 ml of dichloromethane and 1.0 g (3.6 mmol) of redistilled diphenoxyphosphinyl isocyanate (C$_6$H$_5$O)$_2$P(O)NCO dissolved in 20 ml of dichloromethane were successively added dropwise to an icy-cold solution of 1.77 g (3.54 mmol) of Pivampicillin in 20 ml of dichloromethane. The reaction mixture was stirred for another 30 minutes whereupon 25 ml of a 0.1 mol phosphate buffer of pH 7.5 were added. The layers were separated and the water-layer was additionally extracted two times with 50 ml volumes of dichloromethane. The waterlayer was discarded and the combined organic layers were twice washed with cold water, dried over anhydrous magnesium sulfate, vacuum filtered, treated with activated carbon, filtered employing filter-aid and concentrated in vacuum to small volume. n-hexane was added till a solid precipitate appeared whereupon the solvent was completely removed in vacuo. After drying in vacuo, 2.6 g (at about 95%) of the above named ester was obtained. According to thin-layer chromatograms, IR— and PMR spectra, the final product was virtually pure.

IR (KBr-disc, values in cm$^{-1}$): ± 3250, 3065, 2975, 2935 (sh), 1790, 1760, 1720 (sh), 1670 (with shoulders), 1590, ± 1530, 1490, 1460 (sh), 1370, 1290, ± 1250 (sh), ± 1215 (sh), 1195, 1165, 1120, 1055, 1030, 1015, ± 970, 780 and 695.

PMR (CDCl$_3$, 60 Mc, TMS, δ-values in ppm): 1.17 (s, 9H); 1.35 and 1.40 (6H); 4.34 (s, 1H); a 5H absorption area from about 5.3 to about 5.9 consisting of an AB-q at 5.76 (width 0.22, J≈5.3 cps) and a multiplet, * an about 17H absorption area from about 6.95 to 7.9 (including 2 NH doublets at about 7.6).

*upon addition of a small amount of DCO$_2$D the multiplet changed to a AB-q (J≈4.2 cps) and a singlet.

Pivaloyloxymethyl D-6-[α-{3-(hydroxy(ethoxy) phosphinyl) ureido}-benzlcarbonamido]-penicillanate (ester of compound of Example 26)

Employing anhydrous conditions, a solution of 1.5 g (9 mmol) of Cl(C$_2$H$_5$O)P(O)NCO in 30 ml of dichloromethane was added dropwise to a solution of 4.5 g (9 mmol) of Pivampicillin and 1 ml of pyridine in 30 ml of dichloromethane at −65° to −70°C. The reaction mixture was stirred for another 2 hours at −70°C whereupon the cooling-bath was removed and stirring was continued until the temperature was about 0°C. The reaction mixture was poured out in iced water of pH 7.0 and a small volume of ethyl acetate was added whereupon the mixture was concentrated in vacuo until the organic solvent was removed. Toluene and sodium bicarbonate were added until at pH 8.0 the product was dissolved in the aqueous-layer for the main part. The layers were separated, the organic layer was discarded and the remaining aqueous-layer was acidified to pH 1.0 in the cold. The desired product was subsequently incompletely extracted with ethyl acetate. The extracts were combined, treated with activated carbon, dried over anhydrous magnesium sulfate and concentrated in vacuo to a small volume. Addition of n-hexane resulted in the precipitation of a solid, which was collected by filtration, washed with hexane and dried in vacuo to obtain 1.0 g (18%) of the above named ester with an estimated 90% purity. The final product contained a small amount of water.

IR (ibidem): ± 3500, about 3300–3350, 2980, 1790, 1760, ± 1650 (with shoulders), about 1530–1555, 1490, 1460, 1370, 1280–1310, ± 1240, 1215, 1170, 1120, 1055, 1040 (sh), ± 990, 780 and 705.

PMR (CDCl$_3$ and a small amount of d$_6$-DMSO, 60 Mc, TMS, δ-values in ppm): about 1.2 (12H); 1.43 and 1.5 (6H); about 3.95 (centre of multiplet, 2H); 4.40 (s, 1H); 5H absorption area from about 5.25 to 6.0 (including AB-q) centered at 5.78 (width 0.23, J≈5.3 cps), at least 9H absorption area from about 6.9 to 8.7 (including a multiplet at about 7.25).

Method II

Pivaloyloxymethyl D-6-[α-(aminosulfonylamino)-benzylcarbonamido]penicillanate (ester of the compound of Example 18)

A partial solution of 1.7 g (3.65 mmol) of potassium D-6-α-(aminosulfonylamino) -benzylcarbonamido penicillanate, 0.6 g (4 mmol) of t-butylcarbonyloxymethyl choride and 0.85 g (5 mmol) of potassium iodide in 140 ml of dry acetone was refluxed for 5.5 hours. The main part of the solvent was removed in vacuo and the remaining reaction mixture was poured in an icy-cold mixture of 25 ml of water and 25 ml of ethyl acetate at pH 7.0. The layers were separated and the aqueous-layer was twice extracted with 10 ml of ethyl acetate. The aqueous-layer was discarded and the combined extracts were washed with a small volume of water, treated with activated carbon, dried over anhydrous magnesium sulfate and completely evaporated. The residual oil was triturated with cyclohexane until the oil solidified and the solid was collected by filtration, washed with cyclohexane and dried in vacuo to obtain 1.5 g (about 75%) of the above named ester with an estimated 90% purity (according to PMR and TLC).

IR (ibidem): about 3250-3340, 3050 (sh), 2960, 2920, ± 1775, ± 1750, 1680, 1520, 1455, ± 1350, 1325, 1160, 1115, 1030, 985 and 700.

PMR (CDCl$_3$, 60 Mc, TMS, δ-values in ppm): 1.19 (9H); 1.42 and 1.50 (6H); 4.39 (1H); a 7H absorption area from about 5.0 to 5.9 to which participate a doublet at about 5.2 (J″≈7.2 cps), a doublet with centre at 5.41 (J≈4.2 cps), a quartet with centre at 5.56 (J≈4.2 cps, J′≈7 cps) and a AB-q with centre at 5.78 (width 0.23 ppm, J$_{AB}$≈5.3 cps); 6.25 (d, J″≈7.2 cps, about 1H); about 7.3 (6H).

Pivaloyloxymethyl D-6-[α-{3-(sulfo) ureido}-benzylcarbonamido]penicillanate (ester of the compound of Example 17)

A solution of 0.5 g of sodium D-6-[α -3-(sulfo) ureido benzylcarbonamido]-penicillanate and 0.6 g of t-butylcarbonyloxymethyl chloride in 10 ml of dry HMPA (hexamethyl phosphonyl triamide) was stirred for 10 hours at room temperature resulting in a virtually quantative conversion to the ester according to thin-layer chromatograms. The reaction mixture was poured into an icy-cold mixture of water and ethyl acetate at pH 6.0 and the layers were separated and the aqueous-layer was additionally extracted with ethyl acetate. The aqueous-layer was discarded and the combined organic extracts were repeatedly washed with small volumes of iced water at pH 8.3 to remove HMPA. The extract was treated with activated carbon, dried over anhydrous magnesium sulfate and evaporated in vacuo. The residual oil was triturated with light petroleum ether which effected solidification of the oil. The solid was collected by filtration and extensively dried in vacuo to obtain 0.25 g (about 40%) of the above named ester which was essentially pure, but contained 1/3 mole of HMPA per mole of penicillin ester.

IR (ibidem): ± 3550, 3300-3350, 2970, 2940, 1785, 1755, 1680-1695, ± 1520,1370, 1135 (sh), 1120, 1035, 990 and 700.

PMR (ibidem): 1.19 (s, 9H); ± 1.45 (narrow doublet, 6H); 4.41 (s, 1H); a 5H absorption area from about 5.1 to 6.0, consisting of a doublet at 5.2 (J≈7.5 cps), a multiplet and an AB-q with centre at 5.78 (width 0.22 ppm, J$_{AB}$≈5.5 cps); an about 8H absorption area from about 6.8 to 7.8; about 9.8 (broad, about 0.5H).

EXAMPLE 32

Sodium D-6-[α-{3-(benzylaminosulfonyl)-ureido}-benzylcarbonamido]-penicillanate

A suspension of 7 g (20 mmol) of D(-) ampicillin in 60 ml of dichloromethane was reacted in the usual fashion with 4.8 ml (20 mmol) of BSA. The resulting solution was cooled down to −65°C whereupon a solution of 2 ml (slightly more than 20 mmol) of chloro sulfonyl isocyanate in 20 ml of dichloromethane was added dropwise at −60° to −65°C. The solution was stirred for another 10 min. at −65°C whereupon 7.5 ml (70 mmol) of benzylamine were added dropwise at −60° to −65°C followed by 1 hour additional stirring at −60°C. The reaction mixture was poured into 250 ml of iced water of pH 7.0 and the mixture was concentrated in vacuo. The resulting solution in water was extracted with 30 ml of diethyl ether at pH 7.0 and the ethereal extract was discarded. The water-layer was acidified to pH 3.5 and was repeatedly extracted with a 9:1 mixture of diethyl ether and ethyl acetate. The combined extracts were washed once with a small volume of iced water of pH 2.5 and once with neutral water. The extract was treated with activated carbon, dried over anhydrous magnesium sulfate, and concentrated in vacuo to small volume. Addition of sodium α-ethylcapronate gave the above named sodium salt in a yield of 5.2 g (about 40%) of nearly pure product (according to PMR and TLC).

IR (KBr-disc, values in cm$^{-1}$): about 3200-3500 (broad and intensive), 3070, 3050, 2980, 2940, 1775, 1680-1700, 1615, 1520-1540, 1500, 1340, 1260, 1170, 1140 and 710.

PMR (d$_6$-DMSO, 60 Mc, DSS, δ-values in ppm): 1.42 and 1.54 (6H); 4.0(s) and 4.05(s) together 3H; about 5.35 (multiplet) and 5.6 (d, J≈7 cps) together 3H; from about 6.7 to 7.7 (12-13H); 8.8 (d, J≈7 cps, 0.8H).

EXAMPLE 33

Sodium D-6-[α-{3-(5-methyl-1,2,4-oxadiazol-3-yl-methylaminosulfonyl)-ureido}-benzylcarbonamido]-penicillanate Employing reaction conditions as in Example 32, a reaction was performed between 20 mmol of D(-) ampicillin, 20 mmol of BSA, about 20 mmol of chlorosulfonyl isocyanate and 50 mmol of 5-methyl-1,2,4-oxadiazol-3-yl-methylamine. Under these conditions, the conversion of the intermediate with the 1,2,4-oxadiazol-methylamine to the desired pencillin did not progress further than about 40%. In the isolation procedure, the desired compound and part of the by-product were extracted together at pH 4.2 with a 1:1 mixture of diethyl ether and ethyl acetate and 5.5 g of a mixture of the sodium salts were obtained from this extract. This mixture was separated by chromatography through an ion exchange column (IRA-68 (chlorine form), pyridine/acetic acid of pH 4.8) and the by-product was eluted first. The fractions with the desired product were combined, evaporated in vacuo at 0°C and the residue was dissolved in water. The solution in water was acidified to pH 3.2 followed by extraction with ethyl acetate to isolate 1.8 g of the nearly pure above named sodium salt.

IR (KBr-disc, values in cm$^{-1}$): 3200-3400, ± 3050, 2970, 2935, 1770, ± 1680, 1590-1610 (very intensive), 1515-1540, 1495 (sh), 1460 (sh), 1400, 1375 (sh), 1320-1340, 1270,1170, 1135. 920, 730 and 710.

PMR (about 5:1 mixture of d$_6$-DMSO and DCO$_2$D, 60 Mc, DSS, δ-values in ppm): 1.45 and 1.55 (6H); 2.51 (s, 3H); 4.25 (2 close singlets, 3H); 5.47 (centre of 0.23 ppm wide AB-q, J≈4.2 cps) and 5.57 (s) together 3H; 7.4 (5H).

EXAMPLE 34

Sodium D-6-[α-{3-(benzyloxy(ethoxy)phosphinyl)-ureido}-benzylcarbonamido]-penicillanate A solution of crude benzyloxy(ethyloxy)phosphinyl isocyanate [($C_6H_5CH_2O$) ($C_2H_5O$)P(O)-NCO] in 30 ml of dry dichloromethane was prepared by reaction of 30 mmol of crude benzyloxy(ethoxy) phosphinylamide [($C_6H_5CH_2O$) ($C_2H_5O$)P(O)—$NH_2$] with phosgene in toluene in the presence of pyridine followed by in vacuo removal of solvents. According to an IR spectrum, the solution contained approximately 20 mmol of the isocyanate. In the mean time, a solution was prepared in the usual manner starting from 7.0 g (20 mmol) of D(−) ampicillin, 5.0 ml of BSA and 30 ml of dichloromethane. This solution was cooled down to 0°C whereupon the solution of the isocyanate was added in 5 minutes and according to thin-layer chromatograms, ampicillin was about two thirds converted into the desired penicillin. The reaction mixture was poured in iced water of pH 7.0, followed by in vacuo removal of dichloromethane. Ethyl acetate was added and the pH lowered to 3.5. The layers were separated and extraction was continued until the greatest part of the penicillin was extracted. The combined extracts were washed with iced water, dried over anhydrous magnesium sulfate, concentrated in vacuo to small volume whereupon sodium α-ethylcapronate was added, etc to obtain 8.0 g (62%) of the above named sodium salt in good state of purity.

IR (KBr-disc, values in $cm^{-1}$): ± 3470, 3300–3400, 3040–3070, 2980, 2930, 1770, ± 1675, 1610, ± 1530 (with shoulders), 1460, 1400, 1380 (sh), 1330, 1220–1260, 1170, 1140, 1030–1060, 990 (sh), 930, 780 (sh), 745 and 710.

PMR ($d_6$-DMSO, 60 Mc, DSS, δ-values in ppm): 1.23 (centre of two close triplets, δν≈0.8 cps, J≈7.0 cps); 1.44 (s) and 1.55 (s) all together 9H; about 3.95 (centre of multiplet and 4.06 (s) together 3H; 5.02 (centre of two close doublets, δν≈1 cps, J≈7.3 cps, 2H); about 5.35 (multiplet) and 5.60 (d, J≈8 cps) together 3H; about 7.35 (10); 7.85 (d, J≈8 cps, about 0.8H); about 8.7 (broad) and 9.05 (d, J≈7.5 cps) together 1.5H).

Starting from 20 mmol of D(−) ampicillin and an about equivalent amount of crude ($C_6H_5CH_2O$) ($C_6H_5$)P (O)NCO, the reaction was performed at 15°–20°C and about a 50% conversion of D(-) ampicillin was reached according to thin-layer chromatography. The desired penicillin was extracted from water at pH 3.7 by means of ethyl acetate to obtain 6.4 g (about 50%) of sodium D-6-[α-{3-(benzyloxy(phenyl)phosphinyl]-ureido}-benzylcarbonamido]-penicillanate in good state of purity.

IR (ibidem): ± 3500, 3300–3400, 3060, 2975, 2940, 1770, ± 1670, 1610, 1555(sh), 1530, 1460, 1445, 1405, 1380(sh), ± 1330, ± 1230, 1170 (sh). 1140, 1060 (sh), 1045–1005, 975 (sh), 920, ± 750 and 705.

PMR (ibidem): 1.45 and 1.56 (6H); 4.10 (s, 1H); 5.05 (centre of 2 doublets, δν≈2.8 cps, J≈7.7 cps, 2H); about 5.35 (multiplet) and 5.57 (d, J≈8 cps) together 3H; fromm about 6.95 to 8.1 (about 16H); about 8.8 (broad) and 9.05 (d, J≈7 cps) together about 1.5H.

Starting from 70 mmol of D(−) ampicillin and an about equivalent amount of crude ($C_6H_5CH_2O)_2$.P(O)NCO, the reaction was performed at 0°C. After hydrolyzation of the reaction product at pH 7.0, the water-layer was first purified by extractions with ethyl acetate at pH 7.0. The desired penicillin was obtained by extractions at pH 3.7 with ethyl acetate to effect 39.7 g (about 57%) of sodium D-6-[α-{3-(dibenzyloxy phosphinyl)-ureido}-benzylcarbonamido]-penicillanate. IR (ibidem): ± 3500, ± 3380 (sh), 3300–3350, 3050, 2970, 1770, 1670 with shoulders at ± 1710, ± 1685 and 1655, ± 1610, 1550 (sh), 1520–1535, 1500 (sh), 1460, 1400, 1315–1335, 1220–1265, 1165 (sh), 1140, 1095 (sh), 1055 (sh), 1035, 1015 (sh), 980 (sh), 935, 740 and 705.

PMR (ibidem): 1.45 and 1.56 (6H); 4.01 (s, 1H); 5.06 (d, J≈7.5 cps, 4H); about 5.35 (multiplet) and 5.63 (d, J≈8 cps) together 3H; about 7.3 (15H); 8.15 (d, J≈8 cps, 0.8H); about 9.0 (broad s and d with J≈7.5 cps; about 1.3H).

Starting from 25 mmol of D(−) ampicillin and an about equivalent amount of crude ($C_6H_5CH_2O$) ($C_2H_5$)P(O)NCO, the reaction was performed at 0°C and the desired penicillin was extracted from water at pH 4.2 with ethyl acetate. Before the preparation of the sodium salt, the combined extracts were washed first with acetic acid/acetate buffer of pH 4.62 to remove a degradation product. 4.4 g (about 22%) of sodium D-6-[α-{3-(benzyloxy(ethyl)phosphinyl)-ureido}-benzylcarbonamido]-penicillanate were isolated in a good state of purity (according to TLC and PMR).

IR (ibidem): ± 3500, 3200–3400, 3050, 2980, 2945 (sh), ± 1770, 1655–1675 with shoulders at 1710 and 1695, 1610, 1510–1560, 1460, 1410, 1365 (sh), ± 1330, 1260, 1185–1230, 1140, 1170(sh), 1095 (sh), 1060 (sh), 1015, 920, 860, 840, 740 and 705.

PMR (ibidem): a very complicated, 11H absorption area from about 0.7 to 2.2 including singlets at 1.43 and 1.55; 3.97 (s, 1H); 4.95 (centre of 2 doublets, δν≈4.3 cps, J≈7.7 cps, 2H); about 5.25 (multiplet) and 5.57 (d, J≈7.5 cps) together 3H; about 7.3 (10H); about 7.95 (d, J≈7.5 cps, about 0.8H); about 8.7 (broad) and 8.95 (d, J≈7 cps) together about 1.5H.

Starting from 20 mmol of D(−) ampicillin and an about equivalent amount of benzyloxy(diethylamino)-phosphinyl isocyanate [($C_6H_5CH_2O$) ($C_2H_5)_2$N P(O)NCO], the reaction was performed at 0°C and the desired penicillin was extracted from water at pH 3.5 with ethyl acetate. 3.5 g (about 26%) of sodium D-6-[α-{3-(benzyloxy(diethylamino)phosphinyl-ureido}-benzylcarbonamido]-penicillanate of about 90% purity was isolated.

IR (KBr-disc, values in $cm^{-1}$): 3200–3500, 3050, 2980, 2945, 2880, 1770, 1560–1580, 1610, 1570 (sh), 1530, 1460, 1405, 1390, 1330, ± 1235, ± 1210, 1185 (sh), 1140, 1045, 1015 (sh), 970, 910, 740, and 705.

PMR (about 6:1 mixture of $d_6$-DMSO and $DCO_2D$, 60 Mc, DSS, δ-values in ppm): about 1.05 (2 close triplets, 6H); 1.44 and 1.58 (6H); about 2.75 to 3.35 (extended multiplet, 4H); 4.27 (s, 1H); 4.97 (d, J≈7.5 cps, 2H); 5.35 to 5.58 (AB-q, J≈4.1 cps) and 5.60 (s) together 3H; about 7.4 (10H). The spectrum of a solution in $d_6$-DMSO alone showed NH doublets at about 7.85 and 9.05 and a broad NH absorption at about 8.7.

EXAMPLE 35

Disodium salt of D-6-[α-{3-hydroxy(ethoxy)phosphinyl-ureido}-benzylcarbonamido]-penicillananic acid This penicillin was also prepared by the method in Example 26. According to another method, the compound is prepared directly as its disodium salt by a smooth reduction of the compound described in Example 34.

1.84 g (about 3 mmol) of sodium D-6-[α-{3-(benzyloxy (ethoxy)phosphinyl)-ureido}-benzylcarbonamido]-penicillanate and 0.25 g (3 mmol) of sodium bicarbonate were dissolved in a mixture of 30 ml of ethanol and 5 ml of water and to the magnetically stirred solution, 1.7 g of 10% palladized carbon were added whereupon hydrogen was passed over the surface of the solution (at atmospheric pressure) at room temperature. The mixture slowly disengaged carbon dioxide and the reduction was completed after 3 hours. The mixture was vacuum filtered with filter said and the filtrate was evaporated in vacuo. The oily residue, weighed 1.5 g and was dissolved in ethanol (96%), whereupon acetone was added resulting in the precipitation of a solid. In order to remove a small impurity, the solid was stirred with absolute ethanol in which the impurity did not dissolve. After the desired product had completely dissolved, undissolved material was removed by filtration and the filtrate was evaporated in vacuo. After extensive drying in vacuo, the colorless above named disodium salt weighed 1.37 g (about 80%) and was at least 95% pure.

IR (KBr-disc, values in cm$^{-1}$): 3300–3400, ± 3060, 2980, 2940 (sh), 1775, ± 1660 with shoulders (very intensive), ± 1610, 1595 (sh), ± 1540, 1460, 1400, 1380, 1310–1350, 1220–1250, 1175, 1140, 1090, 1040, 965, 900, 860, 790, 740 and 710.

In this case, the conditions of the reduction were slightly changed in order to obtain the disodium salt as well as the mono sodium salt. 0.7 g (1.08 mmol) of the compound of Example 34 were dissolved in 25 ml of ethanol and 1 g of 10% palladized carbon were added whereupon hydrogen was introduced or 2 hours. The reaction product was filtered and the filtrate was evaporated in vacuo. The residue was triturated with ethyl acetate, filtered and dried in vacuo, Yield 0.57 g (about 90%) of the mono sodium salt of D-6-[α-{3-(hydroxy(-phenyl)phosphinyl)-ureido}-benzylcarbonamido]-penicillanic acid of about 90% purity. The corresponding disodium salt was prepared by dissolution of the mono sodium salt in absolute ethanol whereupon the calculated amount of sodium α-ethylcapronate was added followed by the introduction of ethyl acetate.

IR of the disodium salt (ibidem): about 3350–3450, 3060, 2980, 2940 (sh), 1770, ± 1690 (sh), 1660 (very intensive), 1640 (sh), 1610, ± 1530 (with shoulders), ± 1500 (sh), ± 1470, 1445, 1410, 1380, 1320–1340, ± 1215, 1145, 1060, 1040 (sh), 1015 (sh), 900, ± 860, 760, 730 and 710.

PMR of the mono sodium salt (d$_6$-DMSO, 60 Mc, DSS, δ-values in ppm): 1.43 and 1.57 (6H); 4.24 (s, 1H); 5.45 (centre of multiplet) and 5.55 (d, J≈7.5 cps) together 3H; about 6.9 to 8.0 (10H); 8.65 (d, J≈7.5 cps, about 0.7H); 9.05 (d, J≈7 cps, about 0.7H).

2.03 g (3 mmol) of the third compound prepared in Example 34 and 0.51 g (6 mmol) of sodium bicarbonate were almost completely dissolved in a mixture of 50 ml of water and 10 ml of ethanol. 2 g of 10% palladized carbon were added whereupon a slow stream of hydrogen was passed over the surface of the suspension for 24 hours and during the reduction, the temperature was maintained at 0°C. Thin-layer chromatography indicated a virtually quantitative and almost complete conversion to the desired compound. At the end of the reduction, the pH was 7.0 and the mixture was filtered with filter-aid. The filtrate was evaporated in vacuo and 40 ml of absolute ethanol were added to the moist oily residue. The resulting solid was collected by filtration, washed with absolute ethanol and dried in vacuo to obtain 1.7 g (more than 90) of practically pure trisodium salt of D-6-[α-{3-(dihydroxyphosphinyl)-ureido}-benzylcarbonamido]-penicillanic acid.

IR (ibidem): about 3250–3450, 2970, 2935 (sh), 1770, 1680 (sh), 1655 (very intensive), 1590, 1545–1565, 1500, 1470 (sh), 1455, 1405, 1385 (sh), 1375 (sh), 1325, 1290, 1255, 1220, 1135, 1095, 1040, 990, 900, 850, 795, 740 and 700. PMR* (about 8:1 mixture of d$_6$-DMSO and DCO$_2$D, 60 Mc, DSS, δ-values in ppm): 1.44 and 1.57 (6H); 4.16 (s, 1H); about 5.4 (centre of multiplet) and about 5.55 (doublet partially developed into singlet) together 3H; 7.35 (5H); about 7.8 (unexchanged residue of NH-doublet); about 9.0 (ibidem).

*Dissolution of the compound in d$_6$-DMSO alone was insufficient.

6.8 g (11.4 mmol) of the fourth compound prepared in Example 34 was dissolved in a mixture of 50 ml of water and 125 ml of ethanol and 0.96 (11.4 mmol) of sodium bicarbonate and 5 g of 10% palladized carbon were added to the solution whereupon for 5 hours, a slow stream of hydrogen was passed over the surface of the stirred suspension at room temperature. The reaction mixture was filtered through filter-aid and with the help of added benzene, the filtrate was evaporated in vacuo. The residue was partly dissolved by addition of absolute ethanol whereby the undissolved part solidified. The dissolved part was subsequently precipitated by the addition of dry acetone to obtain 5.85 g (more than 90%) of 90–95% pure disodium salt of D-6-[α-{3-(hydroxy(ethyl)phosphinyl)-ureido}-benzylcarbonamido -penicillanic acid.

IR (ibidem): 3200–3400, ± 3600 (sh), 2970, 2940 (sh), 1760, 1740–1765, 1600, 1520–1545, ± 1495 (sh), 1445, 1400, 1370(sh), 1320–1340, ±1240, 1180, 1130 (sh), 1060, 890, 855, 730 and 700.

PMR* (about 6:1 mixture of d$_6$-DMSO and DCO$_2$D, 60 Mc, DSS, δ-values, in ppm): a very complicated 11H absorption area from about 0.7 to 2.2 including singlets at 1.46, at 1.58; 4.23 (s, 1H); about 5.3 to 5.7 (multiplet 3H); 7.35 (about 5H); about 8.1 (remainder of a NH-doublet).

*Dissolution of the compound in d$_6$-DMSO alone was insufficient.

0.96 g (1.5 mmol) of the fifth compound prepared in Example 34 and 0.13 g (1.5 mmol) of sodium bicarbonate were dissolved in 25 ml of 96% ethanol and after 1.2 g of 10% palladized carbon were added, a slow stream of hydrogen was passed for 20 hours over the surface of the suspension. During the reduction, the temperature was maintained at 0°C during the first 5 hours while room temperature was applied furtheron. Activated carbon was added and the reaction mixture was filtered through filter-aid. The filtrate was evaporated in vacuo and the residue was treated with dry acetone till the product solidified. Ethyl acetate was added and the solid was collected by filtration to obtain 0.69 g of the disodium salt of D-6-[α-{3-(hydroxy diethylamino)-phosphinyl-ureido}-benzylcarbonamido]-penicillanic acid. Since the product was somewhat impure, it was stirred with 75 ml of absolute ethanol until most complete dissolution. After filtration, the filtrate was concentrated in vacuo to about 20 ml whereupon 30 ml of dry acetone was added. The precipitated solid was collected by filtration to obtain 0.22 g of at least 90% pure product.

IR (KBr-disc, values in cm$^{-1}$): 3200–3500, 3050, 2970, 2935 (sh), 2870, 1665, 1680 (sh), 1600–1660, 1520–1540, 1495 (sh), 1440, 1370–1405, 1325, 1220, 1135, 1070, 1040 (sh), 940, 890, 850, 740, 700.

PMR (about 4:1 mixture of d$_6$-DMSO and DCO$_2$D, 60 Mc, δ-values in ppm, DSS): 1.0 (t, J ≈ 6.5 cps, 6H); 1.47 and 1.59 (6H); about 2.75 to 3.3 (extended multiplet, 4H); 4.25 (s, 1H); 5.36 to 5.58 (AB-q, J≈4.1 cps) and 5.6 (s) together 3H; about 7.35 (5H).

The compound did not dissolve sufficiently in d$_6$-DMSO alone.

EXAMPLE 36

Sodium D-6-[α-{3-(3,4-dimethyl-1-oxo-3-phospholene-1-yl)-ureido}-benzylcarbonamido]-penicillanate Employing anhydrous conditions, the reaction of 0.7 g (2 mmol) of D(—) ampicillin with 0.48 ml of BSA in 10 ml of dichloromethane was performed in the usual manner. Earlier, 1.7 g (10 mmol) of 3,4-dimethyl-1-oxo-1-chloro-3-phospholene were dissolved in a mixture of 45 ml of benzene and 5 ml of acetonitrile and about 5 mg of 1,2-dinitro-benzene and 1.3 g (20 mmol) of sodium cyanate were added to this solution. The resulting mixture was refluxed for 8 hours and the mixture was cooled down to room temperature followed by filtration in a nitrogen atmosphere. The filtrate was evaporated in vacuo and the residue was dissolved in 10 ml of dichloromethane. According to an IR spectrum, this solution contained about 3 mmol of the desired 3,4-dimethyl-1-oxo-3-phospholene-1-yl-isocyanate. This solution was added at —70°C to the solution of ampicillin. Immediately after the dropwise addition had been completed, the ice-bath was removed. After the reaction mixture had attained 0°C, it was poured into iced water of pH 7.0. Dichloromethane was removed from the mixture by concentration in vacuo and the remaining solution in water was purified by extractions with ether at pH 7.0. Subsequently, the solution was saturated with sodium chloride and the pH was lowered to pH 3.0. The desired compound was extracted with ethyl acetate and the compound was isolated as its sodium salt in the usual manner to obtain 1.0 g (about 90%) of the practically pure above named sodium salt.

IR (KBr-disc, values in cm$^{-1}$): ±3200–3500 (very intensive), 3050, 2970, 2915, 1760, 1660, 1600, ± 1530, 1470, 1400, 1320, 1240, 1190, 1150 (sh), 1035, 910 and 700. PMR (d$_6$-DMSO, 60 Mc, DSS, δ-values in ppm): 1.44 (s); 1.54 (s) and 1.68 (slightly broad s) together 12H; from 2.2 to 2.85 (4H); 3.95 (s, 1H); about 5.35 (multiplet) and about 5.55 (doublet, J≈8 cps) together 3H; 7.35 (5H); about 8.25 (unsharp d, about 1H); 8.95 (unsharp q, about 1H) and about 9.45 (broad s, about 0.7H).

EXAMPLES 37

Capsules containing as active ingredient, a penicillin or cephalosporin prepared in the foregoing examples, were prepared in the usual way. The components of these capsules are listed below:

| | |
|---|---|
| Active compound | 150 – 500 mg |
| Potassium bicarbonate | 100 – 300 mg |
| Magnesium stearate | 2 – 10 mg |
| Lactose | q.s. for 1 capsule |

These capsules may be used for oral administration.

EXAMPLE 38

Tablets containing as active ingredient, a penicillin or cephalosporin prepared in the foregoing examples, were prepared in the usual way. The compounds of the tablets are listed below:

| | |
|---|---|
| Active compound | 125 – 500 mg |
| Polyvinylpyrrolidone | 5 – 30 mg |
| Amylum maidis | 100 – 300 mg |
| Magnesium stearate | 1 – 20 mg |
| Lactose | q.s. for 1 tablet |

These tablets may be used for oral administration

EXAMPLE 39

From the penicillins and cephalosporins prepared in the foregoing examples, a dry powder for injection was prepared in the usual way. A quantity of 100 to 200 mg of the sterile sodium salt of the concerning compound was aseptically introduced into a vial suitable for injectable compositions under a nitrogen atmosphere. The vials were closed with rubber plates which were fixed in their position by aluminum joint rings to eliminate the exchange of gases or the penetration of microorganisms. Before use, the powder is dissolved in a suitable amount of sterile and pyrogen-free water.

EXAMPLE 40

From the penicillins and cephalosporins prepared in the foregoing examples, syrups were prepared by mixing the following ingredients:

| | | | |
|---|---|---|---|
| Active compound | 1.5 | – | 6 g |
| Sodium carboxymethylcellulose | 0.06 | – | 0.600 g |
| Sodium saccharinate | 0.1 | – | 1 g |
| Methyl p-hydroxybenzoate | 0.06 | | g |
| Strawberry flavor | 0.1 | – | 5 g |
| Amaranth | 0.010 | | g |
| Saccharose | 30. | | g |
| Water added to a volume of | 60 | | ml |

These prepared syrups may be used for oral administration.

PHARMACOLOGICAL STUDY

Typical compounds of the invention are:

| | |
|---|---|
| IA | D-6-[α-{3-(diethoxyphosphinyl)-thioureido}benzylcarbonamido]-penicillanic acid, |
| IB | D-6-[α-{3-(diethoxyphosphinyl)-ureido}-benzylcarbonamido]-penicillanic acid, |
| IC | D-6-[α-{3-(diethoxyphosphinothioyl)-thioureido}-benzylcarbonamido]-penicillanic acid, |
| ID | D-6-[α-{3-(diethoxyphosphinothioyl)-ureido}-benzylcarbonamido]-penicillanic acid, |
| IIA | D-6-[α-{3-(diphenoxyphosphinyl)-thioureido}-benzylcarbonamido]-penicillanic acid, |
| IIB | D-6-[α-{3-(diphenoxyphosphinyl)-ureido}-benzylcarbonamido]-penicillanic acid, |
| IIC | D-6-[α-{3-(diphenoxyphosphinothioyl)-thioureido}-benzylcarbonamido]-penicillanic acid, |
| IID | D-6-[α-{3-(diphenoxyphosphinothioyl)-ureido}-benzylcarbonamido]-penicillanic acid, |
| IIIA | D-6-[α-{3-(bis(dimethylamino)phosphinyl)-thioureido}-benzylcarbonamido]-penicillanic acid, |
| IIIB | D-6-[α-{3-(bis(dimethylamino)phosphinyl)-ureido}-benzylcarbonamido]-penicillanic acid, |
| IIIC | D-6-[α-{3-(bis(dimethylamino)phosphinothioyl)-thioureido}-benzylcarbonamido]-penicillanic acid, |
| IIID | D-6-[α-{3-(bis(dimethylamino)phosphinothioyl)-ureido}-benzylcarbonamido]-penicillanic acid, |
| IVA | D-6-[α-{3-(diphenylphosphinothioyl)-thioureido}-benzylcarbonamido]-penicillanic acid, |
| IVB | D-6-[α-{3-(diphenylphosphinothioyl)-ureido}-benzylcarbonamido]-penicillanic acid, |
| IVC | D-6-[α-{3-(diphenylphosphinyl)-thioureido}-benzylcarbonamido]-penicillanic acid. |

-continued

| | |
|---|---|
| IVD | D-6-[α-{3-(diphenylphosphinyl)-ureido}-benzylcarbonamido]-penicillanic acid, |
| VA | D-6-[α-{3-(diemthylphosphinothioyl)-thioureido}-benzylcarbonamido]-penicillanic acid, |
| VB | D-6-[α-{3-(dimethylphosphinyl)-ureido}-benzylcarbonamido]-penicillanic acid, |
| VC | D-6-[α-{3-(dimethylphosphinothioyl)-ureido}-benzylcarbonamido]-penicillanic acid, |
| VI | D-6-[α-{3-(ethoxysulfonyl)-ureido}-benzylcarbonamido]-penicillanic acid, |
| VII | D-6-[α-{3-(phenylaminosulfonyl)-ureido}-benzylcarbonamido]-penicillanic acid, |
| VIII | D-6-[α-{3-(diisopropylaminosulfonyl)-ureido}-benzylcarbonamido]-penicillanic acid, |
| IX | D-6-[α-{3-(isopropylaminosulfonyl)-ureido}-benzylcarbonamido]-penicillanic acid, |
| X | D-6-[α-{3-(ethoxycarbonylmethylaminosulfonyl)-ureido}-benzylcarbonamido]-penicillanic acid, |
| XI | D-6-[α-{3-(pyrid-3-ylaminosulfonyl)-ureido}-benzylcarbonamido]-penicillanic acid, |
| XII | D-6-[α-{3-(5-methylisoxazol-3-yl-aminosulfonyl)-ureido}-benzylcarbonamido]-penicillanic acid, |
| XIII | D-6-[α-{3-(3,4-dimethylisoxazol-5-yl-aminosulfonyl)-ureido}-benzylcarbonamido]-penicillanic acid, |
| XIV | D-6-[α-{3-(morpholino-sulfonyl)-ureido}-benzylcarbonamido]-penicillanic acid, |
| XV | D-6-[α-{3-(ethoxycarbonylhydrazinosulfonyl)-ureido}-benzylcarbonamido]-penicillanic acid, |
| XVI | D-6-[α-{3-(aminosulfonyl)-ureido}-benzylcarbonamido]-penicillanic acid, |
| XVII | D-6-[α-{3-(sulfo)-ureido}-benzylcarbonamido]-penicillanic acid, |
| XVIII | D-6-[α-(aminosulfonylamino)-benzylcarbonamido]-penicillanic acid, |
| XIX | D-6-[α-(ethoxycarbonylaminosulfonylamino)-benzylcarbonamido]-penicillanic acid, |
| XX | D-6-[α-(phenoxycarbonylaminosulfonylamino)-benzylcarbonamido]-penicillanic acid, |
| XXI | D-6-[α-{1-(dimethylamino)-ethylideneamino-sulfonamido}-benzylcarbonamido]-penicillanic acid, |
| XXII | D-6-[α-{3-(diethylmercaptophosphinyl)-ureido}-benzylcarbonamido]-penicillanic acid, |
| XXIII | D-6-[α-{1-(methylpyrrolidin-2-ylidene)-aminosulfonamido}-benzylcarbonamido]-penicillanic acid, |
| XXIV | D-6-[α-{3-(dianilinophosphinyl)-ureido}-benzylcarbonamido]-penicillanic acid, |
| XXV | D-6-[α-{3-(anilinoethoxyphosphinyl)-ureido}-benzylcarbonamido]-penicillanic acid, |
| XXVI | D-6-[α-{3-(hydroxy(ethoxy)phosphinyl)-ureido}-benzylcarbonamido]-penicillanic acid, |
| XXVIIA | D-7-[α-{3-(diethoxyphosphinyl)-ureido}-benzylcarbonamido]-desacetoxycephalosporanic acid, |
| XXVIIB | D-7-[α-{3-(diethoxyphosphinothioyl)-ureido}-benzylcarbonamido]-desacetoxycephalosporanic acid, |
| XXVIIC | D-7-[α-{3-(diphenoxyphosphinyl)-ureido}-benzylcarbonamido]-desacetoxycephalosporanic acid, |
| XXVIII | D-6-[α-{3-(ethoxycarbonylhydrazino(ethoxy)phosphinyl)-ureido}-benzylcarbonamido]-penicillanic acid, |
| XXIX | D-6-[α-{(ethoxy)(N'-phenylureido)-phosphinylamino}-benzylcarbonamido]-penicillanic acid, |
| XXXA | D-7-[α-{3-(hydroxy(ethoxy)phosphinyl)-ureido}-benzylcarbonamido]-desacetoxycephalosporanic acid, |
| XXXB | D-7-[α-{3-(hydroxy(isobutoxy)phosphinyl)-ureido}-benzylcarbonamido]-desacetoxycephalosporanic acid, |
| XXXII | D-6-[α-{3-(benzylaminosulfonyl)-ureido}-benzylcarbonamido]-penicillanic acid, |
| XXXIII | D-6-[α-{3-(5-methyl-1,2,4-oxadiazol-3-yl-methylamino-sulfonyl)-ureido}-benzylcarbonamido]-penicillanic acid, |
| XXXIVA | D-6-[α-{3-(benzyloxy(ethoxy)phosphinyl)-ureido}-benzylcarbonamido]-penicillanic acid, |
| XXXIVB | D-6-[α-{3-(benzyloxy(phenyl)phosphinyl)-ureido}-benzylcarbonamido]-penicillanic acid, |
| XXXIVC | D-6-[α-{3-(dibenzyloxyphosphinyl)-ureido}-benzylcarbonamido]-penicillanic acid, |
| XXXIVD | D-6-[α-{3-(benzyloxy(ethyl)phosphinyl)-ureido}-benzylcarbonamido]-penicillanic acid, |
| XXXIVE | D-6-[α-{3-(benzyloxy(diethylamino)phosphinyl)-ureido}-benzylcarbonamido]-penicillanic acid, |
| XXXVA | D-6-[α-{3-(hydroxy(ethoxy)phosphinyl)-ureido}-benzylcarbonamido]-penicillanic acid, |
| XXXVB | D-6-[α-{3-(hydroxy(phenyl)phosphinyl)-ureido}-benzylcarbonamido]-penicillanic acid, |
| XXXVC | D-6-[α-{3-(dihydroxyphosphinyl)-ureido}-benzylcarbonamido]-penicillanic acid, |
| XXXVD | D-6-[α-{3-(hydroxy(ethyl)phosphinyl)-ureido}-benzylcarbonamido]-penicillanic acid, |
| XXXVE | D-6-[α-{3-(hydroxy(diethylamino)-phosphinyl)-ureido}-benzylcarbonamido]-penicillanic acid, |
| XXXVI | D-6-[α-{3-(3,4-dimethyl-1-oxo-3-phospholene-1-yl-)-ureido}-benzylcarbonamido]-penicillanic acid, | the corresponding cephalosporanic acid derivatives and/or salts (including those having one or more moles of water of crystallization) and pharmaceutically acceptable esters derived from these acids.

The antibiotic activity against Gram-positive and Gram-negative microorganisms of these penicillanic acid and cephalosporanic acid derivatives was determined by the following agar serial dilution test:

A stock solution of the compound at 2,000 ug/ml was prepared in a sterile suitable vehicle and twofold dilutions were made with sterile 1/20 mol phosphate buffer pH 6.5 ($KH_2PO_4$—NaOH) 1 ml quantities of each dilution were incorporated in 19 ml brain-heart infusion agar in sterile Petri dishes. The hardened surface was inoculated with test organisms and incubated for 24 hours at 37°C. The minimal inhibitory concentration of the compound (MIC), i.e. the least concentration of antibiotic that completely inhibits the growth of the test organism, was expressed in μg/ml. The MIC values of the compounds, identified by the numbers above are reported in the following tables.

The MIC values in the following tables between brackets have been determined by the micro serial dilution test, which was carried out as follows:

Two drops of a stock solution of a known concentration of the test compound (antibiotic) were brought into the first hole of a test plate with 9 numbered holes by means of a sterile Pasteur pipette. After rinsing this pipette three times with a physiological NaCl-solution, two drops of a stock solution of the test organism in a culture medium, were brought in all the holes except the hole 8. In the first hole the solution of the test compound had been diluted to half the concentration, then, after stirring the liquid in the first hole and adding two drops of this mixture to the second hole and so on until hole 8, dilutions of the test compound solution were obtained in geometrical progression.

The hole 9 contained no antibiotic and served for checking the growth of the test organism in a blank medium. The test plate was incubed at 30°C or 37°C for about 18 hours.

TABLE

| IA | IB | MIC's in μg/ml IC | ID | IIA | IIB | IIC | IID | IIIA | IIIB | IIIC | IIID | Bacteria | Strain |
|---|---|---|---|---|---|---|---|---|---|---|---|---|---|
| | | | | | | | | | | | | Gram Pos. | |
| 0.25 | 0.5 | 3 | 0.25 | 0.25 | 0.06 | 0.5 | 0.25 | 1 | 1 | 1 | 0.12 | Bacillus subtilis | ATCC 6633 |
| 3 | 1.5 | 3 | 1 | 0.25 | 0.06 | 1.5 | 0.25 | 1.5 | 1 | 1 | 0.5 | Staphylococcus aureus | A 321 |
| 100 | 12.5 | >100 | 25 | 25 | 6 | 12.5 | 25 | 12.5 | 25 | 25 | 3 | | A 355') |
| 50 | 12.5 | 25 | 6 | 25 | 3 | 12.5 | 3 | 12.5 | 12.5 | 12.5 | 3 | | A 2000 |
| 1.0 | 6 | 12.5 | 3 | 3 | 0.25 | 3 | 1 | 3 | 6 | 3 | 3 | | A 2001 |
| 0.25 | 6 | 0.5 | 0.03 | 0.12 | 0.05 | 0.3 | — | 0.12 | 0.06 | 0.06 | 0.03 | Streptococcus haemolyticus | A 266 |
| 100 | 12.5 | 50 | 3 | 50 | 0.25 | 25 | 1.5 | 12.5 | 6 | 12.5 | 1.5 | Streptococcus faecalis | L 80 |
| 0.5 | 0.5 | 3 | 0.3 | 0.5 | 0.06 | — | 0.25 | 0.5 | 1.5 | — | 0.12 | Diplococcus pneumoniae | L 54 |
| | | | | | | | | | | | | Gram neg. | |

TABLE-continued

| IA | IB | IC | ID | IIA | IIB | IIC | IID | IIIA | IIIB | IIIC | IIID | Bacteria | Strain |
|---|---|---|---|---|---|---|---|---|---|---|---|---|---|
| >100 | 100 | — | — | >125 | 125 | — | — | 125 | — | — | (8) | Haemophilus influenzae | A 1030 |
| 125 | 90 | 6 | 0.5 | 0.25 | 0.03 | 1.5 | — | 1.0 | 0.12 | 1 | 0.5 | Brucella meltitensis | A 488 |
| 1 | 3 | 6 | 1.5 | 12.5 | 3 | 1.5 | 3 | 1.5 | 0.5 | 0.5 | 0.75 | Pasteurella multocida | A 723 |
| 0.5 | 1.0 | >100 | 25 | 100 | 25 | 100 | 12.5 | — | 100 | 50 | 25 | Klebsiella pneumoniae | A 809 |
| >100 | — | >100 | 12.5 | 12.5 | 25 | 100 | 12.5 | 25 | 12.5 | 50 | 6 | Salmonella dublin | P 43 |
| — | — | >100 | 25 | 100 | 50 | 100 | 50 | 50 | 50 | 50 | 25 | Salmonella typhimurium | R 127 |
| 6 | 25 | >100 | 50 | 100 | 50 | 100 | 25 | 50 | 50 | 50 | 25 | Escherichia coli | U 20 |
| 100 | 50 | 25 | 6 | 12.5 | 0.12 | 12.5 | 3 | 3 | 3 | 3 | 3 | Shigella equirulis | T 3 |
| 0.5 | 3 | >100 | >100 | >100 | >100 | >100 | 100 | >100 | >100 | >100 | >100 | Pseudomonas aeruginosa | H 10 |
| >100 | 50 | >100 | 100 | 100 | 50 | >100 | 25 | 25 | 50 | 100 | 50 | | 2396 |
| >100 | 50 | >100 | 100 | 100 | 50 | >100 | 25 | 25 | 50 | >100 | 100 | Wyeth | A 1058 |
| >100 | 3 | >100 | 12.5 | 25 | 6 | 25 | 12.5 | 1.5 | 3 | 25 | (0.6) | Proteus rettgeri | A 821 |
| 50 | 25 | >100 | 12.5 | 25 | 12.5 | 50 | 12.5 | 12.5 | 25 | >100 | 12.5 | Proteus mirabilis | H 3 |
| 3 | 12.5 | 25 | 6 | 3 | 3 | 3 | 6 | 1.5 | 3 | 100 | 3 | | L 93 |
| — | 6 | >100 | 25 | 12.5 | 12.5 | 25 | 12.5 | 6 | 25 | >100 | 12.5 | | A 1200 |
| 25 | 6 | >100 | 100 | >100 | 50 | 25 | 100 | 100 | 100 | >100 | 25 | Proteus morganii | 2241 |

| IVA | IVB | IVC | IVD | VA | VB | VC | VI | VII | VIII | IX | Bacteria | Strain |
|---|---|---|---|---|---|---|---|---|---|---|---|---|
| | | | | | | | | | | | Gram pos. | |
| 0.5 | 0.1 | 0.5 | 0.3 | 0.12 | 0.25 | 3 | 0.25 | 1 | 1 | 1.5 | Bacillus subtilis | ATCC 6633 |
| 6 | 0.3 | 3 | 0.8 | 1 | 0.5 | 3 | 1.5 | 1 | 1 | 1.5 | Staphylococcus aureus | A 321 |
| 50 | 6 | 50 | 6 | 3 | 3 | 1.5 | 50 | 25 | 12.5 | 25 | | A 355') |
| 12.5 | 3 | 12.5 | 3 | 3 | 3 | 1.5 | 12.5 | 12.5 | 12.5 | 25 | | A 2000 |
| 25 | 3 | 12.5 | 1.5 | 1.5 | 1.5 | 1.5 | 6 | 3 | 6 | 12.5 | | A 2001 |
| 0.25 | 18 | 0.1 | 0.03 | 0.06 | 0.03 | 0.03 | 0.25 | 1 | 0.25 | 0.75 | Streptococcus haemolyticus | A 266 |
| 50 | 1.5 | 12.5 | 3 | 1.5 | 1 | 1.5 | 25 | 25 | 6 | 25 | Streptococcus faecalis | L 80 |
| 0.5 | >100 | 0.5 | >100 | <1.5 | 0.25 | <1.5 | 6 | 1 | 1 | 12.5 | Diplococcus pneumoniae | L 54 |
| | | | | | | | | | | | Gram neg. | |
| — | 125 | 2 | 125 | 12.5 | >100 | 1.5 | — | — | — | — | Haemophilus influenzae | A 1030 |
| 12.5 | 0.5 | 0.5 | 0.8 | 3 | 1.5 | 1 | 0.06 | 1 | 12.5 | 0.12 | Brucella meltitensis | A 488 |
| 3 | 0.8 | 3 | 0.8 | 0.25 | 0.12 | 1.5 | >100 | 25 | 6 | 0.5 | Pasteurella multocida | A 723 |
| >100 | 50 | >100 | 50 | 100 | 50 | 50 | >100 | 25 | 25 | 100 | Klebsiella pneumoniae | A 809 |
| >100 | 12.5 | 50 | 6 | 100 | 25 | 6 | 6 | 12.5 | 25 | 12.5 | Salmonella dublin | P 43 |
| >100 | 50 | 100 | 25 | 100 | 25 | 25 | 25 | 25 | 100 | 50 | Salmonella typhimurium | R 127 |
| >100 | 25 | 25 | 12.5 | 50 | 25 | 12.5 | 12.5 | 12.5 | 25 | 25 | Escherichia coli | U 20 |
| >100 | 3 | 12.5 | 3 | 3 | 1.5 | 1.5 | 6 | 1 | 3 | 12.5 | Shigella equirulis | T 3 |
| >100 | >100 | >100 | 100 | >100 | >50 | >100 | 100 | 50 | 100 | >100 | Pseudomonas aeruginosa | H 10 |
| >100 | 50 | >100 | 50 | 100 | 25 | 25 | 25 | 25 | 50 | >100 | | 2396 |
| >100 | 100 | >100 | 50 | >100 | 50 | 100 | 25 | 50 | 50 | >100 | Wyeth | A 1058 |
| >100 | 1.5 | 6 | 3 | 6 | 1.5 | 4 | 1.5 | 1.5 | 25 | 0.75 | Proteus rettgeri | A 821 |
| >100 | 12.5 | 50 | 12.5 | 25 | 25 | 12.5 | 12.5 | 3 | 100 | 12.5 | Proteus mirabilis | H 3 |
| >100 | 3 | 6 | 6 | 3 | 1.5 | 1.5 | 1.5 | 1.5 | 12.5 | 0.75 | | L 93 |
| >100 | 25 | 50 | 12.5 | 12.5 | 12.5 | 12.5 | 1.5 | 3 | 50 | 6 | | A 1200 |
| >100 | 50 | >100 | >100 | 100 | 100 | 25 | >100 | 25 | 100 | 100 | Proteus morganii | 2241 |

| X | XI | XII | XIII | XIV | XV | XVI | XVII | XVIII | XIX | XX | Bacteria | Strain |
|---|---|---|---|---|---|---|---|---|---|---|---|---|
| | | | | | | | | | | | Gram pos. | |
| 1 | 0.25 | 1.5 | 0.5 | 1.5 | 1 | 0.5 | 0.5 | 0.5 | 1 | 0.12 | Bacillus subtilis | ATCC 6633 |
| 3 | 3 | 3 | 1 | 6 | 1.5 | 3 | 3 | 0.5 | 3 | 1 | Staphylococcus aureus | A 321 |
| 25 | 12.5 | 25 | 25 | 25 | 12.5 | 25 | 12.5 | 12.5 | 50 | 25 | | A 355') |
| 12.5 | 12.5 | 25 | 12.5 | 25 | 12.5 | 25 | 12.5 | 6 | 12.5 | 12.5 | | A 2000 |
| 12.5 | 12.5 | 12.5 | 3 | 12.5 | 6 | 6 | 12.5 | 3 | 6 | 3 | | A 2001 |
| 0.25 | 0.12 | 1.5 | 0.12 | 3 | 0.5 | 0.12 | 0.12 | 0.06 | 0.25 | 0.06 | Streptococcus haemolyticus | A 266 |
| 25 | 6 | 25 | 12.5 | 25 | 25 | 6 | 25 | 1.5 | 25 | 6 | Streptococcus faecalis | L 80 |
| 1.5 | 0.25 | — | 1.5 | — | 9 | — | 0.25 | — | 3 | 0.25 | Diplococcus pneumoniae | L 54 |
| | | | | | | | | | | | Gram neg. | |
| — | — | — | — | — | 1.5 | — | — | — | — | — | Haemophilus influenzae | A 1030 |
| 0.5 | 6 | 1.5 | — | 1.0 | 0.5 | 0.12 | 0.25 | 0.12 | 1 | 0.5 | Brucella melitensis | A 488 |
| 0.25 | 0.5 | 1.5 | 0.12 | 0.25 | 0.25 | 0.5 | 0.12 | 0.5 | 0.5 | 0.5 | Pasteurella multocida | A 723 |
| 100 | >100 | 50 | 100 | 100 | 100 | >100 | 100 | >100 | >100 | >100 | Klebsiella pneumoniae | A 809 |
| 25 | 50 | 12.5 | 25 | 50 | 12.5 | 100 | 6 | 6 | 50 | 25 | Salmonella dublin | P 43 |
| 50 | >100 | 25 | 50 | 100 | 50 | >100 | 50 | 12.5 | 100 | 50 | Salmonella typhimurium | R 127 |
| 25 | >100 | 25 | 12.5 | 50 | 12.5 | 100 | 25 | 12.5 | 100 | 100 | Escherichia coli | U 20 |
| 15 | 12.5 | 1.5 | 1 | 3 | 3 | 6 | 1 | 3 | 3 | 3 | Shigella equirulis | T 3 |
| >100 | >100 | 100 | 100 | 100 | >100 | >100 | 50 | >100 | >100 | >100 | Pseudomonas aeruginosa | H 10 |
| 100 | 50 | 25 | 50 | 50 | 50 | 50 | 25 | 50 | 100 | 100 | | 2396 |
| 25 | 50 | 25 | 25 | 100 | 100 | 50 | 25 | >100 | 50 | 100 | Wyeth | A 1058 |
| <0.75 | 3 | 6 | 3 | 1.5 | 1 | 25 | <0.75 | 1.5 | 3 | 1.5 | Proteus rettgeri | A 821 |
| 1.5 | <0.75 | 6 | 12.5 | 6 | 3 | 50 | 12.5 | 12.5 | 25 | 12.5 | Proteus mirabilis | H 3 |
| <0.75 | 3 | 1.5 | 0.75 | <0.75 | — | 6 | <0.75 | 3 | 1.5 | 0.75 | | L 93 |
| 3 | 12.5 | 1.5 | 6 | 3 | 1.5 | 25 | 3 | 6 | 25 | 6 | | A 1200 |
| 50 | >100 | 50 | 100 | 100 | 6 | >100 | 50 | 25 | >100 | 50 | Proteus morganii | 2241 |

| XXI | XXII | XXIII | XXIV | XXV | XXVI | XXVIIA | XXVIIB | XXIIC | XXVIII | XXIX | XXX |
|---|---|---|---|---|---|---|---|---|---|---|---|
| 0.12 | 0.25 | 0.12 | 0.12 | 1 | 1.5 | 6 | 12.5 | 6 | 0.5 | 0.5 | 25 |
| 1.5 | 0.5 | 1 | 0.25 | 3 | 3 | 6 | 12.5 | 1.5 | 0.5 | 1.5 | 25 |
| 12.5 | 6 | 6 | 3 | 6(11) | 25(45) | 12.5 | 12.5 | 3 | 6 | 6 | 100 |
| 12.5 | 6 | 6 | 3 | 3(15) | 25(22.5) | 12.5 | 12.5 | 1.5 | 6 | 6 | 50 |
| 12.5 | 6 | 3 | 3 | 3(3.7) | 12.5(22.5) | 6 | 12.5 | 1.5 | 3 | 6 | 12.5 |
| 0.12 | 0.06 | 0.06 | 0.03 | 0.06 | 0.25 | 1 | 1 | 1 | 0.06 | 0.12 | 12.5 |
| 3 | 3 | 1.5 | 3 | 6 | 12.5 | >100 | >100 | >100 | 3 | 12.5 | >100 |
| 0.75 | 0.25 | 0.5 | 0.5 | 0.5 | 1.5 | 25 | 6 | 12.5 | 0.5 | 0.5 | >100 |
| (1.8) | (≧125) | (125) | (12) | (93) | (30) | (30) | (60) | (30) | >125 | (4) | (60) |

TABLE-continued

| XXI | XXII | XXIII | XXIV | XXV | XXVI | XXVII A | XXVIIB | XXIIC | XXVIII | XXIX | XXX |
|---|---|---|---|---|---|---|---|---|---|---|---|
| 1.5 | 0.5 | 0.5 | 0.5 | 1.5 | 1.5 | 12.5 | 100 | 25 | 0.5 | 3 | 25 |
| 0.75 | 0.5 | 0.5 | 1.5 | 3 | 0.5 | 12.5 | 25 | 25 | 0.75 | 1.5 | 12.5 |
| 100 | 25 | >100 | 25 | 25 | 50 | 25 | 50 | 100 | >100 | >100 | 50 |
| 25 | 3 | 50 | 12.5 | 12.5 | 6 | 100 | 50 | 100 | 6 | 50 | 50 |
| 100 | 12.5 | 100 | 25 | 25 | 25 | 100 | 100 | >100 | 12.5 | >100 | >100 |
| 100 | 12.5 | 100 | 25 | 25 | 6 | 100 | >100 | >100 | 25 | >100 | >100 |
| 12.5 | 1.5 | 3 | 1.5 | 3 | 1 | 25 | 100 | 12.5 | 1.5 | 12.5 | 12.5 |
| >100 | 100 | >100 | 100 | 100 | 50 | >100 | >100 | >100 | >100 | >100 | >100 |
| 100 | 50 | >100 | 25 | 25 | 12.5 | >100 | >100 | >100 | 25 | 50 | >100 |
| >100 | 50 | >100 | 25 | 25 | 12.5 | >100 | >100 | >100 | 25 | 50 | >100 |
| (0.6) | (0.3) | (0.9) | (0.3) | 3 | (0.06) | 50 | 25 | 50 | (0.9) | 1.5 | 6 |
| 50 | 6 | 50 | 12.5 | 25 | (0.9) | >100 | >100 | >100 | 6 | 50 | 25 |
| 3 | 1.5 | 3 | 0.3 | 6 | (0.12) | 100 | >100 | >100 | 1.5 | 6 | 12.5 |
| 25 | 6 | 12.5 | 6 | 12.5 | (0.45) | >100 | >100 | >100 | 3 | 25 | 100 |
| 25 | 100 | 50 | 25 | 50 | 6 | >100 | >100 | >100 | 50 | 50 | >100 |

Strain
Bacteria
Gram pos.
*Bacillus subtilis* ATCC 6633
*Staphylococcus aureus* A321
           A355')
           A2000
           A2001
*Streptococcus haemolyticus* A266
*Streptococcus faecalis* L80
*Diplococcus pneumoniae* L54
Gram neg.
*Haemophilus influenzae* A1030
*Brucella melitensis* A488
*Pasteurella multocida* A723
*Klebsiella pneumoniae* A809
*Salmonella dublin* P43
*Salmonella typhimurium* R172
*Escherichia coli* U20
*Shigella equirulis* T3
*Pseudomonas aeruginosa* H10
           2396
      Wyeth A1058
*Proteus rettgeri* A821
*Proteus mirabilis* H3
           L93
           A1200
*Proteus morganii* 2241

| XXX B | XXXI A | XXXII | XXXIII | XXXIVA | XXXIVB | XXXIVC | XXXIVD | XXXVA | XXXVB | XXXVC | XXXVI |
|---|---|---|---|---|---|---|---|---|---|---|---|
| 12.5 | 100 | 0.5 | 0.75 | 0.25 | 0.5 | 0.25 | 0.12 | 0.5 | 0.5 | 0.5 | 0.25 |
| 12.5 | 100 | 1 | 6 | 0.5 | 0.75 | 0.75 | 0.75 | 3 | 0.75 | 3 | 0.75 |
| 50 | >100 | 6 | 12.5 | 6 | 3 | 6 | 6 | 25 | 25 | 50 | 6 |
| 25 | >100 | 6 | 12.5 | 6 | 3 | 6 | 3 | 25 | 6 | 50 | 6 |
| 12.5 | >100 | 6 | 12.5 | 6 | 3 | 1.5 | 1.5 | 12.5 | 6 | 50 | 6 |
| 3 |  | 0.25 | 0.5 | 0.06 | 0.06 | 0.25 | 0.25 | 0.5 | 0.25 | 0.75 | 0.12 |
| >100 | >100 | 12.5 | 25 | 6 | 3 | 12.5 | 3 | 12.5 | 12.5 | 12.5 | 6 |
| 12.5 | 50 | 12.5 | 12.5 | 0.25 | 0.12 | 0.5 | 0.25 | 1.5 | 0.5 | 6 | 0.25 |
| (>125) | (≥125) | (23) | (30) | (0.6) | (4) | (0.6) | (125) | (0.23) | (2.5) | (1.2) | (0.6) |
| 50 |  | 1.5 | 3 | 1.5 | 1.5 | 1.5 | 0.5 | 1.5 | 1.5 | 1.5 | 1.5 |
| 12.5 | >100 | 0.5 | 3 | 0.5 | 1.5 | 0.5 | 1.5 | 0.25 | 0.25 | 0.75 | 0.75 |
| 25 | >100 | 12.5 | 50 | 25 | 25 | 25 | 25 | 100 | 25 | 100 | 25 |
| 50 | >100 | 6 | 12.5 | 3 | 12.5 | 12.5 | 12.5 | 3 | 6 | 0.75 | 6 |
| 100 | >100 | 25 | 25 | 12.5 | 25 | 25 | 25 | 12.5 | 25 | 12.5 | 25 |
| 100 | >100 | 6 | 6 | 12.5 | 25 | 6 | 25 | 6 | 12.5 | 3 | 12.5 |
| 6 | >100 | 3 | 12.5 | 6 | 3 | 3 | 3 | 3 | 1.5 | 1.5 | 1.5 |
| >100 | >100 | 100 | 100 | 50 | 50 | 50 | >100 | 50 | 50 | 12.5 | 100 |
| >100 | >100 | 25 | 50 | 25 | 25 | 25 | 100 | 25 | 25 | 6 | 50 |
| >100 | >100 | 12.5 | 12.5 | 50 | 25 | 50 | 50 | 25 | 50 | 1.5 | 50 |
| 3 | >100 | (0.025) | (0.025) | (0.12) | (0.4) | (0.023) | (0.45) | (0.015) | (0.018) | (0.12) | (0.45) |
| >100 | >100 | 6 | 1.5 | 3 | 12.5 | 3 | 12.5 | (0.45) | 3 | (0.9) | 12.5 |
| 25 | >100 | (0.06) | (0.03) | (0.25) | (0.23) | (0.09) | 3 | (0.045) | (0.03) | (0.3) | 1.5 |
| >100 | >100 | 3 | 1.5 | 1.5 | 6 | 3 | 12.5 | (0.12) | 3 | (0.6) | 6 |
| >100 | >100 | 12.5 | 6 | 12.5 | 12.5 | 12.5 | 50 | 6 | 6 | 12.5 | 12.5 |

Strain
Bacteria
Gram pos.
*Bacillus subtilis* ATCC 6633
*Staphylococcus aureus* A321
           A355')
           A2000
           A2001
*Streptococcus haemolyticus* A 1088
*Streptococcus faecalis* L80
*Diptococcus pneumoniae* L54
Gram neg.
*Haemophilus influenzae* A1030
*Brucella suis* A 1088
*Pasteurella multocida* A723
*Klebsiella pneumoniae* A809
*Salmonella dublin* P43
*Salmonella typhimurium* R172
*Escherichia coli* U20
*Shigella equirulis* T3

TABLE-continued

| IA | IB | IC | ID | IIA | IIB | IIC | IID | IIIA | IIIB | IIIC | IIID | Bacteria Strain |
|---|---|---|---|---|---|---|---|---|---|---|---|---|
| | | | | | | | | | | | | MIC's in µg/ml |
| | | | | | | | | | | | | Pseudomonas aeruginosa H10 |
| | | | | | | | | | | | | 2396 |
| | | | | | | | | | | | | Wyeth A 1058 |
| | | | | | | | | | | | | Proteus rettgeri A821 |
| | | | | | | | | | | | | Proteus mirabilis H3 |
| | | | | | | | | | | | | L93 |
| | | | | | | | | | | | | A1200 |
| | | | | | | | | | | | | Proteus morganii 2241 |

| A | B | cepha-zolin | cepha-cetril | ampicil-lin | cepha-logly-cin | carbe-nicil-lin | Strain Bacteria |
|---|---|---|---|---|---|---|---|
| | | | | | | | MIC's in µg/ml |
| | | | | | | | Gram pos. |
| 0.25 | 0.5 | 0.25 | 0.12 | 0.025 | 0.25 | 0.06 | Bacillus subtilis ATCC 6633 |
| 0.75 | 0.75 | 0.25 | 0.75 | 0.1 | 12.5 | 0.75 | Staphylococcus aureus A321 |
| 12.5 | 12.5 | 1.5 | 1.5 | 1.5 | 12.5 | 3 | A355') |
| 6 | 12.5 | 0.75 | 1.5 | 1.5 | 12.5 | 3 | A2000 |
| 6 | 3 | 0.5 | 0.5 | 0.75 | 12.5 | 3 | A2001 |
| 0.12 | 0.25 | 0.12 | 0.5 | — | 0.25 | 0.25 | Streptococcus haemolyticus A1088 |
| 6 | 6 | 12.5 | 12.5 | 0.8 | >100 | 25 | Streptococcus faecalis L80 |
| 0.25 | 0.5 | 0.25 | 0.5 | 0.05 | 6 | 0.5 | Diplococcus pneumoniae L54 |
| | | | | | | | Gram neg. |
| (0.45) | (23) | (15) | (30) | | (125) | (90) | Haemophilus influenzae A1030 |
| 6 | 3 | 6 | 1.5 | — | 50 | 12.5 | Brucella suis A2126 |
| 0.75 | 6 | 1.5 | 6 | 0.2 | 50 | 0.25 | Pasteurella multocida A723 |
| 100 | 100 | 1.5 | 6 | 50 | 6 | >100 | Klebsiella pheumoniae A809 |
| 12.5 | 50 | 1.5 | 12.5 | 0.8 | 12.5 | 1.5 | Salmonella dublin P43 |
| 25 | 100 | 3 | 12.5 | 3 | 12.5 | 6 | Salmonella typhimurium R172 |
| 12.5 | 100 | 1.5 | 6 | 3 | 1.5 | 1.5 | Escherichia coli U20 |
| 25 | 12.5 | 3 | 6 | 0.8 | 3 | | Shigella equirulis T3 |
| 100 | >100 | >100 | >100 | >100 | >100 | 100 | Pseudomonas aeruginosa H10 |
| 50 | 100 | >100 | >100 | 50 | >100 | 25 | 2396 |
| 100 | >100 | >100 | >100 | >100 | >100 | 25 | Wyeth A1058 |
| 1.5 | 3 | (1.2) | 3 | 3 | 1.5 | (0.12) | Proteus rettgeri A821 |
| 12.5 | 100 | 6 | 12.5 | 3 | 25 | (0.6) | Proteus mirabilis H3 |
| 3 | 12.5 | 1.5 | 12.5 | 3 | 3 | (0.3) | L93 |
| 12.5 | 100 | 6 | 12.5 | 3 | 12.5 | (0.45) | A1200 |
| 25 | >100 | 25 | >100 | 12.5 | 100 | 1.5 | Proteus morganii 2241 |

A represents:sodium D-6[α{3 (ethoxy(ethyl)phoshpinyl)ureido} benzylcarbonamido] penicillanate
B represents:sodium D-6[α{-3 (ethoxy(ethyl)phosphinyL)amino} benzylcarbonamido] penicillanate Various modification of the products and methods of the invention may be made without departing from the spirit or scope thereof and it is to be understood that the invention is to be limited only as defined in the appended claims.

We claim:

1. Penicillanic derivatives of the formula

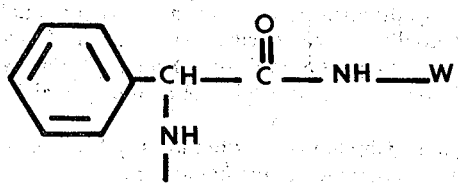

wherein W is a group of the formula

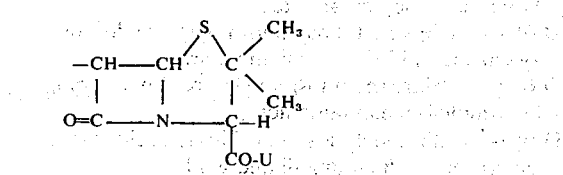

wherein U is —OE, E is select-d from the group consisting of hydrogen, a non-toxic, pharmaceutically acceptable salt-forming cation and a conventional, non-toxic, pharmaceutically acceptable ester-forming group which is known to improve the absorption characteristics of penicillanic acid derivatives after oral administration to warm-blooded animals and Y is a group of the formula

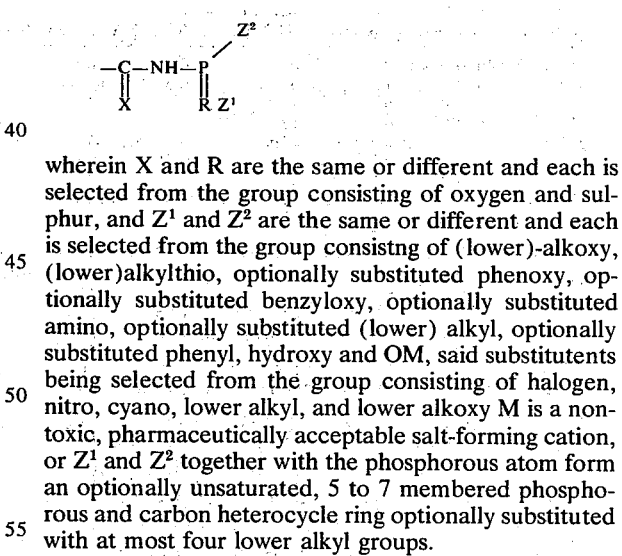

wherein X and R are the same or different and each is selected from the group consisting of oxygen and sulphur, and $Z^1$ and $Z^2$ are the same or different and each is selected from the group consistng of (lower)-alkoxy, (lower)alkylthio, optionally substituted phenoxy, optionally substituted benzyloxy, optionally substituted amino, optionally substituted (lower) alkyl, optionally substituted phenyl, hydroxy and OM, said substitutents being selected from the group consisting of halogen, nitro, cyano, lower alkyl, and lower alkoxy M is a non-toxic, pharmaceutically acceptable salt-forming cation, or $Z^1$ and $Z^2$ together with the phosphorous atom form an optionally unsaturated, 5 to 7 membered phosphorous and carbon heterocycle ring optionally substituted with at most four lower alkyl groups.

2. Penicillanic acid derivatives of claim 1 wherein E is selected from the group consisting of hyrogen, sodium, potassium and ammonium ions and an ester residue of the formula

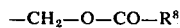

wherein $R_8$ is straight or branched chain alkyl of 1 to 8 carbon atoms optionally substituted by at least one substituent selected from the group consisting of lower alkoxy, lower alkylthio, halo lower alkyl, nitro and halogen.

3. Penicillanic acid derivatives of claim 1 wherein Y is selected from the group consisting of di(lower)alkoxyphosphinylaminocarbonyl, di(lower)alkoxyphosphinothioylaminocarbonyl, diphenoxyphosphinylaminocarbonyl, diphenoxyphosphinothioylaminocarbonyl, di(di(lower)alkylamino)phosphinylaminocarbonyl, di(di(lower)alkylamino)phosphinothioylaminocarbonyl, di(lower)alkylthiophosphinothioylaminocarbonyl, diphenylphosphinylaminocarbonyl, diphenylphosphinothioylaminocarbonyl, di(lower)alkylphosphinylaminocarbonyl, di(lower)alkylphosphinothioylaminocarbonyl, di(anilino)phosphinylaminocarbonyl, anilino-(lower)alkoxyphosphinylaminocarbonyl, hydroxy-(lower)alkoxy-phosphinyl-aminocarbonyl, hydroxy-phenyl-phosphinylaminocarbonyl, hydroxy(lower)alkylphosphinylaminocarbonyl, (lower)alkoxy-benzyloxyphosphinylaminocarbonyl, phenyl-benzyloxyphosphinylaminocarbonyl, lower alkyl-benzyloxyphosphinylaminocarbonyl, dibenzyloxy-phosphinylaminocarbonyl, dihydroxy-phosphinylaminocarbonyl, hydroxy-di(lower)alkylaminophosphinylaminocarbonyl, benzyloxy-di(lower)alkylaminophosphinylaminocarbonyl, di(lower)alkylthiophosphinylaminocarbonyl and (lower)alkoxycarbonylhydrazino-(lower)alkoxy-phosphinylaminocarbonyl, the corresponding phosphinyl (or phosphinothioyl) aminothiocarbonyl and the 3,4-dimethyl-1-oxo-3-phospholene-1-ylaminocarbonyl.

4. Penicillanic acid derivatives of claim 1 selected from the group consisting of D-6-[α-{3-(diethoxyphosphinyl)-thioureido}-benzylcarbonamido]-penicillanic acid, D-6-[α-{3-(diethoxyphosphinyl)-ureido}-benzylcarbonamido]penicillanic acid, D-6-[α-{3-(diethoxyphosphinothioyl)-thioureido}-benzylcarbonamido]-penicillanic acid, D-6-[α-{3-(diethoxyphosphinothioyl)-ureido}-benzylcarbonamido]-penicillanic acid, D-6-[α-{3-(diphenoxyphosphinyl)-thioureido}-benzylcarbonamido]-penicillanic acid, D-6-[α-{3-(diphenoxyphosphinyl)-ureido}-benzylcarbonamido]-penicillanic acid, D-6-[α-{3-(diphenoxyphosphinothioyl)-thioureido}-benzylcarbonamido]-penicillanic acid, D-6-[α-{3-(diphenoxyphosphinothioyl)-ureido}-benzylcarbonamido]-penicillanic acid, D-6-[α-{3-(bis-(dimethylamino)-phosphinyl)-thioureido}-benzylcarbonamido]-penicillanic acid, D-6-[α-{3-(bis-(dimethylamino)-phosphinyl)-ureido}-benzylcarbonamido]-penicillanic acid, D-6-[α-{3-(bis-(dimethylamino)-phosphinothioyl)-thioureido}-benzylcarbonamido]-penicillanic acid, D-6-[α-{3-(bis-(dimethylamino)-phosphinothioyl)-ureido}-benzylcarbonamido]-penicillanic acid, D-6[α-{3-(diphenylphosphinothioyl)-thioureido}-benzylcarbonamido]-penicillanic acid, D-6-[α-{3-(diphenylphosphinothioyl)-ureido}-benzylcarbonamido]-penicillanic acid, D-6[α-{3-(diphenylphosphinyl)-thioureido}-benzylcarbonamido]-penicillanic acid, D-6-[α-{3-(diphenylphosphinyl)-ureido}-benzylcarbonamido]-penicillanic acid, D-6-[α-{3-(dimethylphosphinothioyl)-thioureido}-benzylcarbonamido]-penicillanic acid, D-6-[α-{3-(dimethylphosphinyl)-ureido}-benzylcarbonamido]-penicillanic acid, D-6-[α-{3-(dimethylphosphinothioyl)-ureido}-benzylcarbonamido]-penicillanic acid, D-6-[α-{3-(diethylmercaptophosphinyl)-ureido}-benzylcarbonamido]-penicillanic acid, D-6-[α-{3-(dianilinophosphinyl)-ureido}-benzylcarbonamido]-penicillanic acid, D-6-[α-{3-(anilionethoxyphosphinyl)-ureido}-benzylcarbonamido]-penicillanic acid, D-6-[α-{3-(hydroxy(ethoxy)phosphinyl)-ureido}-benzylcarbonamido]-penicillanic acid, D-6-[α-{3-(ethoxycarbonylhydrazino(ethoxy)phosphinyl)-ureido}-benzylcarbonamido]-penicillanic acid, D-6-[α-{3-(benzyloxy(ethoxy)phosphinyl)-ureido}-benzylcarbonamido]-penicillanic acid, D-6-[α-{3-(benzyloxy(phenyl)phosphinyl)-ureido}-benzylcarbonamido]-penicillanic acid, D-6[α-{3-(dibenzyloxyphosphinyl)-ureido}-benzylcarbonamido]-penicillanic acid, D-6-[α-{3-(benzyloxy(ethyl)phosphinyl)-ureido}-benzylcarbonamido]-penicillanic acid, D-6-[α-{3-(benzyloxy(diethylamino)phosphinyl)-ureido}-benzylcarbonamido]-penicillanic acid, D-6-[α-{3-(hydroxy(ethoxy)phosphinyl)-ureido}-benzylcarbonamido]-penicillanic acid, D-6-[α-{3-(hydroxy(phenyl)phosphinyl)-ureido}-benzylcarbonamido]-penicillanic acid, D-6-[α-{3-(dihydroxyphosphinyl)-ureido}-benzylcarbonamido]-penicillanic acid, D-6-[α-{3-(hydroxy(ethyl)phosphinyl)-ureido}-benzylcarbonamido]-penicillanic acid, D-6[α-{3-(hydroxy(diethylamino)phosphinyl)-ureido}-benzylcarbonamido]-penicillanic acid, and D-6-[α-{3-(3,4-dimethyl-1-oxo-3-phospholene-1-yl)-ureido}-benzylcarbonamido]-penicillanic acid, D-6-[α-{3-(hydroxy(isobutoxy)phosphinyl)-ureido}-benzylcarbonamido]-penicillanic acid, and non-toxic, pharmaceutically acceptable salts and conventional non-toxic, pharmaceutically acceptable esters of said acids which are known to improve the absorption characteristics of penicillanic acid derivatives after oral administration to warm-blooded animals.

5. Penicillanic acid derivatives of claim 4 selected from the group consisting of D-6-[α-{3-(diphenoxyphosphinyl)-ureido}-benzylcarbonamido]-penicillanic acid, D-6[α-{3-(diphenoxyphosphinothioyl)-ureido}-benzylcarbonamido]-penicillanic acid, D-6[α-{3-bis(dimethylamino)phosphinothioyl)-ureido}-benzylcarbonamido]-penicillanic acid, D-6-[α-{3-(diphenylphosphinyl)-ureido}-benzylcarbonamido]-penicillanic acid, D-6[α-{3-(diphenylphosphinothioyl)-ureido}-benzylcarbonamido]-penicillanic acid, D-6-[α-{3-(dimethylphosphinyl)-ureido}-benzylcarbonamido]-penicillanic acid, D-6[α-{3-(dimethylphosphinothioyl)-ureido}-benzylcarbonamido]-penicillanic acid, D-6-[α-{3-(dimethylphosphinothioyl)-thioureido}-benzylcarbonamido]-penicillanic acid, D-6-[α-{3-(hydroxy(ethoxy)phosphinyl)-ureido}-benzylcarbonamido]-penicillanic acid, D-6-[α-{3-(dihydroxyphosphinyl)-ureido}-benzylcarbonamido]-penicillanic acid, D-6-[α-{3-(phenyl(benzyl)phosphinyl)-ureido}-benzylcarbonamido]-penicillanic acid, D-6[α-{3-(dibenzyloxyphosphinyl)-ureido}-benzylcarbonamido]-penicillanic acid,
D-6[α-{3-(ethoxy(benzyloxy)phosphinyl)-ureido}-benzylcarbonamido]-penicillanic acid,
D-6[α-{3-(dianilinophosphinyl)-ureido}-benzylcarbonamido]-penicillanic acid,
D-6[α-{3-(3,4-dimethyl-1-oxo-3-phospholene-1-yl)-ureido}-benzylcarbonamido]-penicillanic acid,
D-6-[α-{3-(hydroxy(phenyl)phosphinyl)-ureido}-benzylcarbonamido]-penicillanic acid,
D6[α-{3-(benzyloxy(ethoxy)phosphinyl)-ureido}benzylcarbonamido]-penicillanic acid
D-6-[α-{3-(ethoxycarbonylhydrazino(ethoxy)phosphinyl)-ureido}-benzylcarbonamido]-penicillanic acid, and non-toxic, pharmaceutically acceptable salts and conventional, non-toxic, pharmaceutically acceptable esters thereof which are known to improve the absorption characteristics of penicillanic acid derivatives after oral administration to warm-blooded animals.

6. A compound of claim 1 selected from the group consisting of D-6-[α-{3-(hydroxy(ethoxy)phosphinyl)-ureido}-benzylcarbonamido]-penicillanic acid and non-toxic, pharmaceutically acceptable salts thereof.

7. A compound of claim 1 selected from the group consisting of D-6-[α-{3-(dihydroxyphosphinyl)-ureido}-benzylcarbonamido]-penicillanic acid and non-toxic, pharmaceutically acceptable salts thereof.

8. A compound of claim 1 selected from the group consisting of D-6[α-{3-hydroxy(ethyl)phosphinyl)-ureido}-benzylcarbonamido]-penicillanic acid and the non-toxic, pharmaceutically acceptable salts thereof.

* * * * *

UNITED STATES PATENT OFFICE
CERTIFICATE OF CORRECTION

Page 1 of 6

Patent No. 3,945,994　　　　　　　　Dated　March 23, 1976

Inventor(s) CORNELIS ADRIANUS BRUYNES, JOHANNES KAREL van der DRIFT

It is certified that error appears in the above-identified patent and that said Letters Patent are hereby corrected as shown below:

| Col. | Line | |
|---|---|---|
| [75] | | Inventors "ander" should be --and-- |
| 6 | 1 | "1" should be --inert-- |
| 6 | 2 | "rang" should be --range-- |
| 6 | 3 | After "anhydrous" insert --con-- |
| 6 | 4 | "prot" should be --protect-- |
| 6 | 5 | "pre" should be --present-- |
| 6 | 10 | After formula insert --XIV-- |
| 6 | 14 | "$Z^{3=}$" should be --$Z^{3*}$-- |
| 6 | 14 | "def" should be --defined-- |
| 6 | 15 | After "converted" insert --into-- |
| 6 | 16 | "org" should be --organic-- |
| 6 | 17 | "solent" should be --solvent-- |
| 6 | 17 | "betw" should be --between-- |
| 6 | 18 | "co" should be --condi-- |
| 6 | 19 | "obta" should be --obtained-- |
| 6 | 22 | "$Z^4$ - H" should be --$Z^{4*}$ - H   XV -- |

UNITED STATES PATENT OFFICE
CERTIFICATE OF CORRECTION

Patent No. 3,945,994  Dated March 23, 1976

Inventor(s) CORNELIS ADRIANUS BRUYNES, JOHANNES KAREL van der DRIFT

It is certified that error appears in the above-identified patent and that said Letters Patent are hereby corrected as shown below:

| Col. | Line | |
|---|---|---|
| 6 | 24 | "$Z^{4=}$" should be --$Z^{4*}$-- |
| 6 | 24 | After "or" insert --is a-- |
| 6 | 25 | "grou" should be --group-- |
| 6 | 26 | After "25°C" insert --and-- |
| 6 | 27 | "in" should be --in the-- |
| 6 | 28 | "org" should be --organic-- |
| 6 | 29 | After "conditions" insert --op- -- |
| 6 | 30 | "protec" should be --protecting-- |
| 6 | 34 | After formula insert --XVI-- |
| 6 | 36 | After "organic" insert --sol-- |
| 6 | 37 | "bet" should be --between-- |
| 6 | 38 | "anhyd" should be --anhydrous-- |
| 6 | 39 | "sc" should be --so ob- -- |
| 6 | 43 | "$Z^{5=}$-H" should be --$Z^{5*}$-H  XVIII-- |
| 6 | 44 | "$Z^{5==}$" should be --$Z^{5*}$-- |
| 6 | 44 | "def" should be --defined-- |

UNITED STATES PATENT OFFICE
CERTIFICATE OF CORRECTION

Patent No. 3,945,994  Dated March 23, 1976

Inventor(s) CORNELIS ADRIANUS BRUYNES, JOHANNES KAREL van der DRIFT

It is certified that error appears in the above-identified patent and that said Letters Patent are hereby corrected as shown below:

| Col. | Line | |
|---|---|---|
| 6 | 45 | After "converted" insert --into-- |
| 6 | 46 | "b" should be --below-- |
| 6 | 47 | After "-80°C" insert --op- -- |
| 6 | 48 | After "agent" insert --such-- |
| 6 | 49 | "u" should be --under-- |
| 6 | 50 | "th" should be --the re- -- |
| 6 | 51 | "re" should be --result- -- |
| 6 | 57 | After formula insert --XVIII-- |
| 6 | 60 | "$Z^{3=}$" should be --$Z^{3*}$-- |
| 6 | 60 | "significanc" should be --significances as-- |
| 6 | 61 | "tem" should be --tempera- -- |
| 6 | 62 | "10°(" should be --10°C de- -- |
| 6 | 63 | After "substituent" insert --$Z^{3*}$,-- |
| 6 | 64 | After acid-binding" insert --agent-- |
| 6 | 65 | "prefe" should be --preferably-- |
| 6 | 66 | "followe" should be --followed by-- |

UNITED STATES PATENT OFFICE
CERTIFICATE OF CORRECTION

Patent No. 3,945,994  Dated March 23, 1976

Inventor(s) CORNELIS ADRIANUS BRUYNES, JOHANNES KAREL van der DRIFT

It is certified that error appears in the above-identified patent and that said Letters Patent are hereby corrected as shown below:

| Col. | Line | |
|---|---|---|
| 6 | 67 | "th" should be --the re- -- |
| 15 | 43 | "D(=)" should be --D(-)-- |
| 20 | 9 | "35 1325" should be --±1325-- |
| 20 | 11 | "60 Mcγ" should be --60 Mcδ-- |
| 20 | 29 | "aat" should be --at-- |
| 20 | 48 | "60 Mcγ" should be --60 Mcδ-- |
| 32 | 6 | "icewater" whould be --ice-water-- |
| 33 | 18 | "(d, J α 6.5 cps" should be (d, J≠6.5 cps-- |
| 34 | 15 | "benzlcarbonamido" should be --benzylcarbonamido-- |
| 37 | 63 | "fromm" should be --from-- |
| 40 | 5 | "(more than 90)" should be --(more than 90%)-- |

UNITED STATES PATENT OFFICE
CERTIFICATE OF CORRECTION

Patent No. 3,945,994   Dated March 23, 1976

Inventor(s) CORNELIS ADRIANUS BRUYNES, JOHANNES KAREL van der DRIFT

It is certified that error appears in the above-identified patent and that said Letters Patent are hereby corrected as shown below:

| Col. | Line | |
|---|---|---|
| 40 | 35 | "bonamido-" should be --bonamido]- -- |
| 41 | 7 | "x" should be --⌿-- |
| 41 | 51&52 | Between 1150 (sh) and 1035 insert --1130 (sh)-- |
| 42 | 20 | "200 mg" should be --2000 mg-- |
| 44 | 7 | --D-7-[α-{3-(diphenoxyphosphinyl)-- "phsophinyl" should be --phosphinyl-- |
| 49 | Under Table | "phosphinylL" should be --phosphinyl-- |

UNITED STATES PATENT OFFICE
CERTIFICATE OF CORRECTION

Patent No. 3,945,994      Dated March 23, 1976

Inventor(s) CORNELIS ADRIANUS BRUYNES, JOHANNES KAREL van der DRIFT

It is certified that error appears in the above-identified patent and that said Letters Patent are hereby corrected as shown below:

Col.   Line

Claims

49    Claim 1      "select-d" should be --selected--

50    Claim 2      "$R_8$" should be --$R^8$--

Signed and Sealed this

Twenty-eighth Day of September 1976

[SEAL]

Attest:

RUTH C. MASON      C. MARSHALL DANN
*Attesting Officer*      *Commissioner of Patents and Trademarks*

UNITED STATES PATENT OFFICE
CERTIFICATE OF CORRECTION

Patent No. 3,945,994      Dated March 23, 1976

Inventor(s) Cornelis Adrianus Bruynes et al.

It is certified that error appears in the above-identified patent and that said Letters Patent are hereby corrected as shown below:

Title page, Item [75], second line after "Inventors"

"Koudekerk ander Rijn; Johannes" should read -- Koudekerk a/d Rijn; Johannes --.

Signed and Sealed this

Fifteenth Day of March 1977

[SEAL]

Attest:

RUTH C. MASON
Attesting Officer

C. MARSHALL DANN
Commissioner of Patents and Trademarks